(12) United States Patent
Bauw et al.

(10) Patent No.: US 6,469,149 B1
(45) Date of Patent: Oct. 22, 2002

(54) PRODUCTION OF ASCORBIC ACID IN PLANTS

(75) Inventors: Guy Jerome Corneel Bauw, Proven-Poperinge (BE); Mark William Davey, Ghent (BE); Jens Ostergaard, Lyngby (DK); Marc Charles Ernest Van Montagu, Brussels (BE)

(73) Assignee: Vlaams Interuniversitair Instituut Voor Biotechnologies, Zwijnaarde (BE)

( * ) Notice: Subject to any disclaimer, the term of this patent is extended or adjusted under 35 U.S.C. 154(b) by 0 days.

(21) Appl. No.: 09/423,468

(22) PCT Filed: May 7, 1998

(86) PCT No.: PCT/EP98/02830

§ 371 (c)(1),
(2), (4) Date: Feb. 15, 2000

(87) PCT Pub. No.: WO98/50558

PCT Pub. Date: Nov. 12, 1998

(30) Foreign Application Priority Data

May 7, 1997 (NL) ............................................. 1006000

(51) Int. Cl.$^7$ ..................... C07H 21/00; C07H 21/04; C12Q 1/68; C12P 21/02; A01N 43/04
(52) U.S. Cl. ................... 536/22.1; 536/23.5; 536/24.31; 435/6; 435/69.5; 514/44; 530/387.1
(58) Field of Search ................... 435/6, 69.5, 69.51, 435/69.52, 320.1, 325; 514/44; 530/387.1, 350, 22.1; 536/23.5, 24.31

(56) References Cited

U.S. PATENT DOCUMENTS

| | | | |
|---|---|---|---|
| 4,259,443 A | | 3/1981 | Danehy ....................... 435/137 |
| 5,599,680 A | * | 2/1997 | Feinberg et al. ............. 435/7.21 |
| 5,736,387 A | * | 4/1998 | Paul et al. .................. 435/320.1 |

FOREIGN PATENT DOCUMENTS

| | | |
|---|---|---|
| WO | WO 85/01745 | 4/1985 |
| WO | WO 93/19193 | 9/1993 |
| WO | WO 96/17944 | 6/1996 |
| WO | WO 96/31115 | 10/1996 |
| WO | WO 97/04100 | 2/1997 |

OTHER PUBLICATIONS

Database WPI, *Cloned DNA including rat L-gulonolactone oxidase-used in recombinant vector for transforming host cells*, Derwent Publications, Ltd. Section Ch, Week 8920, London, GB.

Mitsuru Fukuda et al., *Effect of storage time of potatoes after harvest on increase in the ascorbic acid content by wounding*, Chemical Abstracts, vol. 124, No. 9, 1995, p. 1121.

Kunio Yagi et al., *Expression in Monkey Cells of the Missing Enzyme in L–Asorbic Acid Acid Biosynthesis, L–Gulono–y–Lactone Oxidase*, Biochemical and Biophysical Research Communications, vol. 177, No. 2, Jun. 14, 1991, pp. 659–663.

Y. Minobe et al., *Rice cDNA, partial sequence* (R0642$_{-1A}$), EMBL Database, Rel. 37, Nov. 29, 1993, Accession No. D23947, p. 1.

Jens Ostergaardt et al., *Isolation of a CDNA Coding for L–Galactono–y–Lactone Dehydrogenase, an Enzyme involved in the Biosynthesis of Ascorbic Acid in Plants*, The Journal of Biological Chemistry, vol. 272, No. 48, Nov. 28, 1997, pp. 30009–30016.

Y. Bai et al., *L–Galactono–1, 4–Lactone: Ferricytochrome–c Oxidoreductase (E.C.1.3.2.3) from Peas and its use in a Bioprocess for L–Ascorbic Acid Synthesis*, Biological Chemistry Hoppe–Seyler, vol. 373, No. 9, Sep. 25, 1992, pp. 857–858.

Kazuko Oba, *Purification and Properties of L–Galactano–y–Lactone Dehydrogenase, a Key Enzyme for Ascorbic Acid Biosynthesis, from Sweet Potato Roots*, J. Biochem, vol. 117, 1995, pp. 120–124.

G. Ishii et al., *Biochemical approach to higher ascorbic acid levels in potato breeding*, Chemical Abstracts, vol. 125, No. 15, 1996, p. 698.

Klaus D. Kulbe et al., *Enzymatic Synthesis of L–Ascorbic Acid via D–Uronic Acids: Membrane–Reactor Integrated Recovery of D–Galacturonic Acid from Pectin Hydrolysates*, Annals of the New York Academy of Sciences, vol. 506, 1987, pp. 543–551.

* cited by examiner

Primary Examiner—W. Gary Jones
Assistant Examiner—Arun Chakrabarti
(74) Attorney, Agent, or Firm—Knobbe, Martens, Olson & Bear LLP

(57) ABSTRACT

The present invention relates to a polynucleotide in isolated form, which polynucleotide codes for a protein with the activity of the enzyme L-galactono-γ-lactone dehydrogenase, which polynucleotide comprises at least the L-galactono-γ-lactone dehydrogenase activity-determining parts of the coding part of the nucleotide sequence or a sequence derived therefrom on the basis of the degeneration of the genetic code. The invention further relates to the use of the polynucleotide in the production of transgenic plants, plant cells, or other eukaryotic cells.

22 Claims, 18 Drawing Sheets

```
   1                                                                             gctttcgctggctcaggttcagatcgcctgaactaaacaaaatg
                                                                                                                            M 47    ctccgatcacttctcctccgcctccaacgcccgttcgcttcgaccccattccccttcccgtcagacc
         L  R  S  L  L  L  R  R  S  N  A  R  S  L  R  P  P  F  P  P  L  R  T  L  C  T  S  G  Q  T
 -90

137    ttgactccagcccctccctccaccgccgcctcctccgcgccgattcatcctgcctcagaaaggagttccgtaaatacgccggatac
         L  T  P  A  P  P  P  P  P  P  P  P  I  S  S  A  S  E  K  E  F  R  K  Y  A  G  Y
-60

227    gcagcactcgctctctcctccggcgcgcaacttactctcccctcccgagaacgccaaacacaagaggctcagatcttccga
         A  A  L  A  L  F  S  G  A  A  T  Y  F  S  F  P  F  P  E  N  A  K  H  K  K  A  Q  I  F  R
 -30

317    tacgctcctctcccgaagatctccacaccgtctctaactggagtggtactcacgaggtccagaccttaaccagccggagact
         Y  A  P  L  P  E  D  L  H  T  V  S  N  W  S  G  T  H  E  V  Q  T  R  N  F  N  Q  P  E  T
   1

407    ctcgccgatctcgaagctctcgtcaaggaagctcatgagagaacaggatccgacccgttggatccgtctttcccccaatggatc
         L  A  D  L  E  A  L  V  K  E  A  H  E  K  N  R  I  R  P  V  G  S  G  L  S  P  N  G  I
  30

497    ggtttgtctcgctcgggatggtgaatttggcgctcaagttgacgccattcaagagtatggtctccgaggtgtggataaagaagaagtcgtgtgcaggct
         G  L  S  R  S  G  M  V  N  L  A  L  M  D  K  V  L  E  V  D  K  E  K  K  R  V  R  V  Q  A
  60

587    gggattagggtttcagcagctgttgacgccattcaagagtatggtctagattgcctcctatgatgagcaagtgattggcatgaagcttgtcactcctgct
         G  I  R  V  Q  Q  L  V  D  A  I  Q  E  Y  G  L  T  L  Q  N  F  A  S  I  R  E  Q  Q  I  G
  90

677    ggcatcattcaggttggggcacatggtactgaagacaggtgctagattgcctcctatcttgcctcgatgtggcctggacttgtggagttgttgctgag
         G  I  I  Q  V  G  A  H  G  T  G  A  R  L  P  P  I  D  E  Q  V  I  G  M  K  L  V  T  P  A
 120

767    aagggaactattgagctttctaaggataatgatccggagctcttttcatcttgcatttcatttgcatttttcatttgtcatttggagttgttgctgag
         K  G  T  I  E  L  S  K  D  N  D  P  E  L  F  H  L  A  R  C  G  L  G  G  L  G  V  V  A  E
 150

857    gtcacctccagtgccgttgaaagacaggagctttttggagcacactacgtctccacttacgtctccacttacgtctccacttctg
         V  T  L  Q  C  V  E  R  Q  E  L  L  E  H  T  Y  V  S  T  L  E  E  I  K  K  N  H  K  K  L
 180
```

```
 947  ctctctacaaataagcatgtcaagtacctgtatattccatatactgacacggtcgtggttgttacatgcaacctgtatcaaatggagt
 210   L  S  T  N  K  H  V  K  Y  L  Y  I  P  Y  T  D  T  V  V  V  T  C  N  P  V  S  K  W  S 1037  gggcacctaaggacaaaccaaagtacactacagagaggagctttaaagcatgtccgtgacctgtatagagagcattgttaagtatagg
 240   G  A  P  K  D  K  P  K  Y  T  T  E  E  A  L  K  H  V  R  D  L  Y  R  E  S  I  V  K  Y  R 1127  gtccaggactctagtaagaagactcctgacagtagggagccagactttcattacagagttgagagataagctgattgcc
 270   V  Q  D  S  S  K  K  T  P  D  S  R  E  P  D  I  N  E  L  S  F  T  T  E  L  R  D  K  L  I  A 1217  ctagatccctctcaatgacgttcacgtttggaaaagtgaatcaagctgagtttggaaaaatcagaaggatcagagtaggtgg
 300   L  D  P  L  N  D  V  H  V  G  K  V  N  Q  A  E  F  W  K  K  S  E  G  Y  R  V  G  W 1307  agtgatgaatcctgggctttgactgtggtcaacagtgggtatcagaaactgtttcctgctgaactctcgctaacctagcatg
 330   S  D  E  I  L  G  F  D  C  G  Q  Q  W  V  S  E  T  C  F  P  A  G  T  L  A  K  P  S  M 1397  aaagacctttgagtacatagaacagctgaaagagttgataacaaaagaagcaatacccagcacctctccatagagcagcgttggacaggc
 360   K  D  L  E  Y  I  E  Q  L  K  E  L  I  Q  K  E  A  I  P  A  P  S  P  I  E  Q  R  W  T  G 1487  cgaagtaagagccctatggtcctgcattcagcactgagttctcatggggttggtataatcatgtatctcccgacagca
 390   R  S  K  S  P  M  S  P  A  F  S  T  A  E  E  D  I  F  S  W  V  G  I  H  M  Y  L  P  T  A 1577  gacccctcgccagagaaagcagatcacggatgaatttttccactattgacacaggcaaattgtggaccagtattctgcgtat
 420   D  P  R  Q  R  K  D  I  T  D  E  F  F  H  Y  R  H  L  T  Q  A  K  L  W  D  Q  Y  S  A  Y 1667  gaacattgggctaaaattgagataccaaaggataaagaggaacttgaagccctacaagaaagactcagaaacgattcccggtggatgca
 450   E  H  W  A  K  I  E  I  P  K  D  K  E  E  L  E  A  L  Q  E  R  L  R  K  R  F  P  V  D  A 1757  tacaacaaagcacgaagggagctggacccaaacagaattctcaaacaacatggtgaaaagctctccctgtcctccaagactgcttaa
 480   Y  N  K  A  R  R  E  L  D  P  N  R  I  L  S  N  N  M  V  E  K  L  F  P  V  S  K  T  A  Q
```

FIG. 3C 1847 aaacatttcatcaatagttttttgctccttgaagtaccacttttgaatcctataacgttgcatctacaagtgtttgtaagaagagtg
1937 aagccgatatattggtcacaaaaaagtttacattgagtttactactattttttttttcgcagttcccctgaataaatacttgttgt
2027 tctattcc

FIG. 5A

```
       accgttcgacccgattctcatgcgggacagaaaccaaaggcccaaaactacaagtcta
   1   ------------+------------+------------+------------+------------+------------+    60
       tggcaagctgggctaagagtacgccctgtctttttgttttccggttttgatgttcagat caataaaatttctggttttgttttggttttgaatgtggacaactagttaccaattgtt
  61   ------------+------------+------------+------------+------------+------------+   120
       gttattttaaagaccaaaacaaaccaaaacttacacctgttgatcaatggttaaacaa cattaacaaattactcggctcaaattatgaaaacagaataaatcagggtataatggaa
 121   ------------+------------+------------+------------+------------+------------+   180
       gtaattgttaatgagccgagttaatacttttgtctttattttagtcccatattacctt actttcttaaatcactaaaccgatcctgtacaagaacattccctcaggttcagatcgc
 181   ------------+------------+------------+------------+------------+------------+   240
       tgaaagaatttagtgattgggctaggacatgttcttgtaagggagtccaagtctagcg ctgaagttaaacaaaaaatgctccggtcacttcttctccgacgctccgtcggccattc
 241   ------------+------------+------------+------------+------------+------------+   300
       gacttcaattgtttttttacgaggccagtgaagaagaggctgcgaggcagccggtaag

```
      tctcggaacccctatctccgtcttcatccaccatccgttcctcatttcgcctcatcgtac
301   ------+---------+---------+---------+---------+---------+    360
      agagccttgggatagaggcagaagtaggtggtaggcaaggatgtaaagcggagtagcatg

L  G  T  L  S  P  S  S  S  T  I  R  S  S  F  S  P  H  R  T  - tctctgcaccaccggtcaaacattgacaccaccacgccgccaccgccacgtcctccacc
361   ------+---------+---------+---------+---------+---------+    420
      agagacgtggtggccagtttgtaactgtggtggcggtggcggtgcaggaggtgg

L  C  T  T  G  Q  T  L  T  P  P  P  P  P  P  R  P  P  P  - tccgcctccggccaccgcctcagaagctcaattccgtaaatacgccggatacgcagcact
421   ------+---------+---------+---------+---------+---------+    480
      aggcggaggccgtggcggagtcttcgagttaaggcatttatgcggcctatgcgtcgtga

P  P  P  A  T  A  S  E  A  Q  F  R  K  Y  A  G  Y  A  A  L  - cgctatctttctctggagttgctacctatttctcattccctgagaatgctaaaca
481   ------+---------+---------+---------+---------+---------+    540
      gcgatagagagacctcaacgatggataaagagtaaggtaaggactcttacgatttgt

```
         caagaaggctcaaatcttccgttacgctccttacctgaagatcttcacactgtctctaa
541      ------+---------+---------+---------+---------+---------+    600
         gttcttccgagtttagaaggcaatgcgaggaatggacttctagaagtgtgacagagatt

K  K  A  Q  I  F  R  Y  A  P  L  P  E  D  L  H  T  V  S  N  - ttggagtggtactcatgaggtacagactaggaactttaatcaaccggagaatcttgctga
601      ------+---------+---------+---------+---------+---------+    660
         aacctcaccatgagtactccatgtctgatcctgaaattagttggcctcttagaacgact

W  S  G  T  H  E  V  Q  T  R  N  F  N  Q  P  E  N  L  A  D  - tctcgaagctcttgttaaggaatctcatgagaagaagttaaggattcgtcccgttggatc
661      ------+---------+---------+---------+---------+---------+    720
         agagcttcgagaacaattccttagagtactcttcttcaattcctaagcagggcaacctag

L  E  A  L  V  K  E  S  H  E  K  K  L  R  I  R  P  V  G  S  - gggtctctcgcctaatgggattggtttgtctcgctctgggatggtgaatctggcgcttat
721      ------+---------+---------+---------+---------+---------+    780
         cccagagagcggattacccctaaccaaacagagcgagacctaccactagaccgcgaata

```
781  ggataaagttctagaggtggataaagagaagagagttacggtgcaggctgggattag
     ----+---------+---------+---------+---------+---------+   840
     cctatttcaagatctccacctatttctctcttcaatgccacgtccgaccctaatc

D  K  V  L  E  V  D  K  E  K  K  R  V  T  V  Q  A  G  I  R 841  ggtccagcaattggtgacgccattaaagactatggtcttactcttcagaactttgcctc
     ----+---------+---------+---------+---------+---------+   900
     ccaggtcgttaaccaactgcggtaatttctgataccagaatgagaagtcttgaaacggag

V  Q  Q  L  V  D  A  I  K  D  Y  G  L  T  L  Q  N  F  A  S 901  cattagagagcagcagattggtggtattattcaggtttgcatatgtttctctcccttgtg
     ----+---------+---------+---------+---------+---------+   960
     gtaatctctcgtcgtctaaccaccataataagtccaaacgtatacaaagagaggaacac

I  R  E  Q  Q  I  G  G  I  I  Q  V 961  tgaagtctagggtttgtgaactaatggagaatctgaaacaatttagttgttcgtcttta
     ----+---------+---------+---------+---------+---------+   1020
     acttcagatcccaacactttgattacctcttagactttgttaaatcaacaagcagaaat
```

FIG. 5E

```
      tcttgtgctttgaggttttagagtctatattttgttacgttcaggttggggcacatg
1021  ------+---------+---------+---------+---------+---------+  1080
      agaacacgaaactccaaaatctcagatataaaacaatgcaagtccaaccccgtgtac
         F  V  Y  V  Q  V  G  A  H  G ggacaggtgctagattgcctcctattgatgagcaggtgatcagtatgaagctggttactc
1081  ------+---------+---------+---------+---------+---------+  1140
      cctgtccacgatctaacggaggataactactcgtccactagtcatacttcgaccaatgag
         T  G  A  R  L  P  P  I  D  E  Q  V  I  S  M  K  L  V  T  P ctgCgaaggaAAcaattgaactttcaagagagaaagatccgagctctttcatctagctc
1141  ------+---------+---------+---------+---------+---------+  1200
      gacGcttcccTTgttaacttgaaagttctctctttctaggcctcgagaaagtagatcgag
         A  K  G  T  I  E  L  S  R  E  K  D  P  E  L  F  H  L  A  R gatgtGGCCttggtGGactgGagttgttgctgaggtcaccctccaatgcgttgcaagac
1201  ------+---------+---------+---------+---------+---------+  1260
      ctacaCCGgaaccaCCtgaaCCtcaacaacgactccagtgggaggttacgcaacgttctg
         C  G  L  G  G  L  G  V  V  A  E  V  T  L  Q  C  V  A  R  H
```

FIG. 5F

```
      atgaacttgtgtggaacacacatacgtctcaaacttgcaagaaatcaagaaaatcacaagt
1261  ------+---------+---------+---------+---------+---------+
      tacttgaacaccttgtgtgtatgcagagtttgaacgttcttttagttctttttagtgttca

E  L  V  E  H  T  Y  V  S  N  L  Q  E  I  K  K  N  H  K taagtatcgctaactttcgctatattagtctccatattatggctccagcttagaaaatca
1321  ------+---------+---------+---------+---------+---------+
      attcatagcgattgaaagcgatataatcagaggtataatacgaggtcgaatctttttagt tgctcagtatacgactttcttctggtcagattatcagagaagtatcagattgatgcaag
1381  ------+---------+---------+---------+---------+---------+
      acgagtcatatgctgaaagagaccagtctaatagtctcttcatagtctaactacgttc agcttaaagtttttcacttttagtactgcccatatcattggcatagtgcattctag
1441  ------+---------+---------+---------+---------+---------+
      tcgaatttcaaaaaagtgaaaatcatgacgggtatagtaaaccgtatcacgtaagatc catttgggaatcactccctctactttgaagcaaattgatcccataattggctcagggt
1501  ------+---------+---------+---------+---------+---------+
      gtaacccttagtgaggggagatgaacttcgtttaactagggtatttaaccgagtccca
```

FIG. 5G

```
      ggaacgtttcctaacttttgttttgttctgGctgttcagaaaattgctctctgcAaaca
1561  ------+---------+---------+---------+---------+---------+  1620
      ccttgcaaaggattgaaaacaaacaaagaCCgacaagtcttttaacgagagacgTttgt
                                                   K  L  S  A  N  K agcatgttaagtacctatatattccTtataCcgacacagtcgtggttgtaacatgcaatc
1621  ------+---------+---------+---------+---------+---------+  1680
      tcgtacaattcatggatatataaggAatatGgctgtgtcagcaccaacattgtacgttag
       H  V  K  Y  L  Y  I  P  Y  T  D  T  V  V  V  T  C  N  P ctgtatcaaaatggagtgggccacctaaggacaaaccaaagtacactacagatgaggctg
1681  ------+---------+---------+---------+---------+---------+  1740
      gacatagttttacctcacccggTGGattccTGTttggtttcatgtgatgtctactccgac
       V  S  K  W  S  G  P  P  K  D  K  P  K  Y  T  T  D  E  A  V tAcagcatgtccgtgatctctacagagagagcattgtgaagtataggtatcgttatgctt
1741  ------+---------+---------+---------+---------+---------+  1800
      aTgtcgtacaggcactagagatgtctctcgtaacacttcatatccatagcaatacgaa
       Q  H  V  R  D  L  Y  R  E  S  I  V  K  Y  R
```

FIG. 5H

```
      aagtcttatgtgtaacttgatttctctaatgtggaggactgaatgaatgcaaataatt
1801  ------------------------------------------------------------  1860
      ttcagaatacacattgaactaaagagattacacctcctgacttacttacgttttattaa ttttactatgatgtataggtgtccaggactcctggtaagaagtctcctgacagcagtgagcc
1861  ------------------------------------------------------------  1920
      aaaatgatactacatatcccagtcctgagaccattcttcagaggactgtcgtcactcgg

R  V  Q  D  S  G  K  K  S  P  D  S  S  E  P  — agacatacaggagctttcattacagagttgagagacaaactactgccctgatcctct
1921  ------------------------------------------------------------  1980
      tctgtatgtcctcgaaagtaatgtctcaactctctgtttgatgaacgggaactaggaga

D  I  Q  E  L  S  F  T  E  L  R  D  K  L  L  A  L  D  P  L  — caatgacgttcacgttgcaaagtaaatcaagctgaggcagagttttggaaaaatcagaa
1981  ------------------------------------------------------------  2040
      gttactgcaagtgcaacgtttcattagttcgactccgtctcaaaaccttttttagtctt N  D  V  H  V  g  K  V  N  Q  A  E  E  F  W  K  K  S  E  —
```

```
2041  ggatatagagtaggtggagtgatgaaattctgggctttgactgtgtggtcagcagtgg
      ----------+---------+---------+---------+---------+---------+  2100
      cctatatctcatcccacctcactacttaagaccgaaactgacaccaccagtcgtcacc

G  Y  R  V  G  W  S  D  E  I  L  G  F  D  C  G  G  Q  Q  W gtgtcagaatctttgtttcctgctggaaccctcgcaaccctagcatgaaagacctttgaa
      ----------+---------+---------+---------+---------+---------+  2160
      cacagtcttagaacaaaggacgaccttgggagcggttgggatcgtactttctggaactt

V  S  E  S  C  F  P  A  G  T  L  A  N  P  S  M  K  D  L  E tacatagagagctgaaaaactaatagaaaaggaagcaataccagcacctgctcccaata
      ----------+---------+---------+---------+---------+---------+  2220
      atgtatctctcgacttttgattatctttccttcgttatggtcgtggacgaggttat

Y  I  E  E  L  K  K  L  I  E  K  E  A  I  P  A  P  A  P  I gagcagcgatggacagctcgaagtaagagcccattagtcctgcATTcagcacttcagag
      ----------+---------+---------+---------+---------+---------+  2280
      ctcgtcgctacctgtcgagcttcattctcgggtaatcaggacgTAAgtcgtgaagtctc

```
2281 gatgatatttctcatgggtaactctgttttatgtcgtttatcctccattacttctc
     ----------+---------+---------+---------+---------+---------+ 2340
     ctactataaagagtaccattgagaacaaatacagcaaataggaaggtaaatgaagag
          D   D   I   F   S   W   V 2341 tttgactttcatgaaagtatgaagagatattggtgtcaatctataggaagcttgttt
     ----------+---------+---------+---------+---------+---------+ 2400
     aaactgaaagtactttcatacttctctataaccacagttagatatccttcgaacaaaaca 2401 ggctctgcctttgtggtgggaggaaaacatgtgatatattgatgttaaaatgttcatagac
     ----------+---------+---------+---------+---------+---------+ 2460
     ccgagacggaaacaccacctcctttgtacactatataactacaatttacaagtatctg 2461 aaagaagaaaccgtaaaaatgatgttacatactgtactcttaggtgctgattgtgttt
     ----------+---------+---------+---------+---------+---------+ 2520
     tttcttcttggcattttactacaatgtatgacatgagaatccacgacctaacaacaaa 2521 cacttggtagattttgtgttggccaaccttgttccaacaccgactgtttgccttttt
     ----------+---------+---------+---------+---------+---------+ 2580
     gtgaaccatctaaaaacaacaaccggttggaacaaggtttgtgctgacaaacgaaaaa
```

```
2581  ctctttcaaatgctagtcatctacagttatataatgctacattacatttgtctcaggttg
      ------+---------+---------+---------+---------+---------+  2640
      gagaaagtttacgatcagtagatgtcaatattatacgatgtaatgtaaacagagtccaac
                                                            V  G  -

2641  gtataatcatgtacctcccgacagcagacccctcgccagagaaggacatcacagatgaat
      ------+---------+---------+---------+---------+---------+  2700
      catattagtacatggagggctgtcgtctgggagcggtctcttcctgtagtgtctactta
      I  I  M  Y  L  P  T  A  D  P  R  Q  R  K  D  I  T  D  E  F 2701  tttccactatagacatttgacacagaaacaattgTGGGatcaaTTTTctgcgtatgaac
      ------+---------+---------+---------+---------+---------+  2760
      aaaaggtgatatctgtaaactgtgtctttgttaacACCCtagttAAAAgacgcatacttg
      F  H  Y  R  H  L  T  Q  K  Q  L  W  D  Q  F  S  A  Y  E  H  -

2761  attgggctaaaatTgaggtaatcgtagatttctaatctaaatatgagatTcttgTatct
      ------+---------+---------+---------+---------+---------+  2820
      taacccgatttaActccattagcatctaaagattagatttatactctaAgaacAtaga
      W  A  K  I  E
```

FIG. 5K

```
        taacacacagatacctcattctcacttaactatgTccttctgattcactcacaaaagt
2821    ---------+---------+---------+---------+---------+---------+    2880
        attgtgtctatggtagtaagagtgaattgatacAggaagactaagtgagtgttttca ctctgTatcttaattacattttttctgcttgaactacaactgtcctcattgtgagaagta
2881    ---------+---------+---------+---------+---------+---------+    2940
        gagacAtagaattaatgtaaaaagacgaacttgatgttgacaggagtaacactcttcat agcaaaggaatgagaatctgttgaggtaactatttagagtgtagacaatttctaatgtt
2941    ---------+---------+---------+---------+---------+---------+    3000
        tcgttccctactcttagacaactccattgataaatctcacatctgttaaagattacaa ttctgtttgatatttatataatcagataccaaaagacaaagaagaacttgaagccttaca
3001    ---------+---------+---------+---------+---------+---------+    3060
        aagacaaactataaatatattagtctatggtttctctgtttcttcttgaacttcggaatgt
                 I   P   K   D   K   E   E   L   E   A   L   Q ggcaagaataagaaaacgtttcccagtggatgcataacaaattcctaggatcctcgag
3061    ---------+---------+---------+---------+---------+---------+    3120
        ccgttcttattcttttgcaagggtcacctacgtatgttgtttaaggatcctaggagctc
         A   R   I   R   K   R   F   P   V   D   A   Y   N   K
```

*FIG. 5L*

SEQUENCE LISTING

<160> NUMBER OF SEQ ID NOS: 15

<210> SEQ ID NO 1
<211> LENGTH: 9
<212> TYPE: PRT
<213> ORGANISM: Brassica oleracea
<220> FEATURE:
<221> NAME/KEY: VARIANT
<222> LOCATION: 2
<223> OTHER INFORMATION: Xaa = any amino acid

<400> SEQUENCE: 1

Leu Xaa Asp Gln Tyr Ser Ala Tyr Glu
 1               5

<210> SEQ ID NO 2
<211> LENGTH: 8
<212> TYPE: PRT
<213> ORGANISM: Brassica oleracea

<400> SEQUENCE: 2

Val Asn Gln Ala Glu Ala Glu Phe
 1               5

<210> SEQ ID NO 3
<211> LENGTH: 13
<212> TYPE: PRT
<213> ORGANISM: Brassica oleracea

<400> SEQUENCE: 3

Leu Ile Ala Leu Asp Pro Leu Asn Asp Val His Val Gly
 1               5                  10

<210> SEQ ID NO 4
<211> LENGTH: 8
<212> TYPE: PRT
<213> ORGANISM: Brassica oleracea

<400> SEQUENCE: 4

Tyr Thr Thr Glu Glu Ala Leu Lys
 1               5

<210> SEQ ID NO 5
<211> LENGTH: 4
<212> TYPE: PRT
<213> ORGANISM: Brassica oleracea

<400> SEQUENCE: 5

Trp Thr Gly Arg
 1

<210> SEQ ID NO 6
<211> LENGTH: 7
<212> TYPE: PRT
<213> ORGANISM: Brassica oleracea

<400> SEQUENCE: 6

Gly Thr Ile Glu Leu Ser Lys
 1               5

<210> SEQ ID NO 7
<211> LENGTH: 10
<212> TYPE: PRT
<213> ORGANISM: Brassica oleracea

```
<400> SEQUENCE: 7

Val Asn Gln Ala Glu Ala Glu Phe Trp Lys
 1               5                   10

<210> SEQ ID NO 8
<211> LENGTH: 5
<212> TYPE: PRT
<213> ORGANISM: Brassica oleracea

<400> SEQUENCE: 8

Ile Glu Ile Pro Lys
 1               5

<210> SEQ ID NO 9
<211> LENGTH: 8
<212> TYPE: PRT
<213> ORGANISM: Brassica oleracea
<220> FEATURE:
<221> NAME/KEY: VARIANT
<222> LOCATION: 5
<223> OTHER INFORMATION: Xaa = any amino acid

<400> SEQUENCE: 9

Tyr Ala Pro Leu Xaa Glu Asp Leu
 1               5

<210> SEQ ID NO 10
<211> LENGTH: 11
<212> TYPE: PRT
<213> ORGANISM: Brassica oleracea

<400> SEQUENCE: 10

Ala Pro Leu Pro Asp Leu His Thr Val Ser Asn
 1               5                   10

<210> SEQ ID NO 11
<211> LENGTH: 17
<212> TYPE: PRT
<213> ORGANISM: Brassica oleracea
<220> FEATURE:
<221> NAME/KEY: VARIANT
<222> LOCATION: 1
<223> OTHER INFORMATION: Xaa = any amino acid
<221> NAME/KEY: VARIANT
<222> LOCATION: 9
<223> OTHER INFORMATION: Xaa = any amino acid
<221> NAME/KEY: VARIANT
<222> LOCATION: 11
<223> OTHER INFORMATION: Xaa = any amino acid
<221> NAME/KEY: VARIANT
<222> LOCATION: 16
<223> OTHER INFORMATION: Xaa = any amino acid

<400> SEQUENCE: 11

Xaa Ser Ser Lys Lys Thr Pro Asp Xaa Arg Xaa Pro Asp Ile Asn Xaa
 1               5                   10                  15

Leu

<210> SEQ ID NO 12
<211> LENGTH: 2034
<212> TYPE: DNA
<213> ORGANISM: Brassica oleracea
<220> FEATURE:
<221> NAME/KEY: CDS
<222> LOCATION: (44)...(1846)

<400> SEQUENCE: 12
```

-continued

```
gctttcgctg gctcaggttt cagatcgcct gaactaaaac aaa atg ctc cga tca         55
                                         Met Leu Arg Ser
                                           1 ctt ctc ctc cgc cgc tcc aac gcc cgt tcg ctt cga ccc cca ttt ccc        103
Leu Leu Leu Arg Arg Ser Asn Ala Arg Ser Leu Arg Pro Pro Phe Pro
  5              10                  15                  20 cct ctc cgc act cta tgc act tcc ggt cag acc ttg act cca gcc cct        151
Pro Leu Arg Thr Leu Cys Thr Ser Gly Gln Thr Leu Thr Pro Ala Pro
             25                  30                  35 cca ccg ccg cct cct cct cca ccg ccg att tca tcc tcc gcc tca gaa        199
Pro Pro Pro Pro Pro Pro Pro Pro Ile Ser Ser Ser Ala Ser Glu
         40                  45                  50 aag gag ttc cgt aaa tac gcc gga tac gca gca ctc gct ctc ttc tcc        247
Lys Glu Phe Arg Lys Tyr Ala Gly Tyr Ala Ala Leu Ala Leu Phe Ser
             55                  60                  65 ggc gcc gca act tac ttc tcc ttc ccc ttc ccc gag aac gcc aaa cac        295
Gly Ala Ala Thr Tyr Phe Ser Phe Pro Phe Pro Glu Asn Ala Lys His
     70                  75                  80 aag aag gct cag atc ttc cga tac gct cct ctc ccc gaa gat ctc cac        343
Lys Lys Ala Gln Ile Phe Arg Tyr Ala Pro Leu Pro Glu Asp Leu His
 85                  90                  95                 100 acc gtc tct aac tgg agt ggt act cac gag gtc cag acc agg aac ttt        391
Thr Val Ser Asn Trp Ser Gly Thr His Glu Val Gln Thr Arg Asn Phe
                105                 110                 115 aac cag ccg gag act ctc gcc gat ctc gaa gct ctc gtc aag gaa gct        439
Asn Gln Pro Glu Thr Leu Ala Asp Leu Glu Ala Leu Val Lys Glu Ala
            120                 125                 130 cat gag aag aag aac agg atc cga ccc gtt gga tcc ggt ctt tcc ccc        487
His Glu Lys Lys Asn Arg Ile Arg Pro Val Gly Ser Gly Leu Ser Pro
            135                 140                 145 aat ggg atc ggt ttg tct cgc tcg ggg atg gtg aat ttg gcg ctc atg        535
Asn Gly Ile Gly Leu Ser Arg Ser Gly Met Val Asn Leu Ala Leu Met
        150                 155                 160 gac aag gtc ctc gag gtg gat aaa gag aag aag aga gtc cgt gtg cag        583
Asp Lys Val Leu Glu Val Asp Lys Glu Lys Lys Arg Val Arg Val Gln
165                 170                 175                 180 gct ggg att agg gtt cag cag ctt gtt gac gcc att caa gag tat ggt        631
Ala Gly Ile Arg Val Gln Gln Leu Val Asp Ala Ile Gln Glu Tyr Gly
                185                 190                 195 ctc act ctc cag aac ttt gct tcc att aga gag cag cag att ggt ggc        679
Leu Thr Leu Gln Asn Phe Ala Ser Ile Arg Glu Gln Gln Ile Gly Gly
            200                 205                 210 atc att cag gtt ggg gca cat ggg aca ggt gct aga ttg cct cct atc        727
Ile Ile Gln Val Gly Ala His Gly Thr Gly Ala Arg Leu Pro Pro Ile
            215                 220                 225 gat gag caa gtg att ggc atg aag ctt gtc act cct gct aag gga act        775
Asp Glu Gln Val Ile Gly Met Lys Leu Val Thr Pro Ala Lys Gly Thr
        230                 235                 240 att gag ctt tct aag gat aat gat ccg gag ctc ttt cat ctt gct cga        823
Ile Glu Leu Ser Lys Asp Asn Asp Pro Glu Leu Phe His Leu Ala Arg
245                 250                 255                 260 tgt ggc ctt ggt gga ctt gga gtt gtt gct gag gtc acc ctc cag tgc        871
Cys Gly Leu Gly Gly Leu Gly Val Val Ala Glu Val Thr Leu Gln Cys
                265                 270                 275 gtt gaa aga cag gag ctt ttg gag cac act tac gtc tcc acc ttg gaa        919
Val Glu Arg Gln Glu Leu Leu Glu His Thr Tyr Val Ser Thr Leu Glu
            280                 285                 290 gag atc aag aaa aat cac aaa aag ttg ctc tct aca aat aag cat gtc        967
Glu Ile Lys Lys Asn His Lys Lys Leu Leu Ser Thr Asn Lys His Val
```

-continued

```
              295                 300                 305
aag tac ctg tat att cca tat act gac acg gtc gtg gtt gtt aca tgc    1015
Lys Tyr Leu Tyr Ile Pro Tyr Thr Asp Thr Val Val Val Val Thr Cys
        310                 315                 320 aac cct gta tca aaa tgg agt ggg gca cct aag gac aaa cca aag tac    1063
Asn Pro Val Ser Lys Trp Ser Gly Ala Pro Lys Asp Lys Pro Lys Tyr
325                 330                 335                 340 act aca gag gag gct tta aag cat gtc cgt gac cta tat aga gag agc    1111
Thr Thr Glu Glu Ala Leu Lys His Val Arg Asp Leu Tyr Arg Glu Ser
                345                 350                 355 att gtt aag tat agg gtc cag gac tct agt aag aag act cct gac agt    1159
Ile Val Lys Tyr Arg Val Gln Asp Ser Ser Lys Lys Thr Pro Asp Ser
            360                 365                 370 agg gag cca gac att aac gag ctt tca ttt aca gag ttg aga gat aag    1207
Arg Glu Pro Asp Ile Asn Glu Leu Ser Phe Thr Glu Leu Arg Asp Lys
        375                 380                 385 ctg att gcc cta gat cct ctc aat gac gtt cac gtt gga aaa gtg aat    1255
Leu Ile Ala Leu Asp Pro Leu Asn Asp Val His Val Gly Lys Val Asn
    390                 395                 400 caa gct gag gct gag ttt tgg aaa aaa tca gaa gga tac aga gta ggg    1303
Gln Ala Glu Ala Glu Phe Trp Lys Lys Ser Glu Gly Tyr Arg Val Gly
405                 410                 415                 420 tgg agt gat gaa atc ctg ggc ttt gac tgt ggt ggt caa cag tgg gta    1351
Trp Ser Asp Glu Ile Leu Gly Phe Asp Cys Gly Gly Gln Gln Trp Val
                425                 430                 435 tca gaa act tgt ttt cct gct gga act ctc gct aaa cct agc atg aaa    1399
Ser Glu Thr Cys Phe Pro Ala Gly Thr Leu Ala Lys Pro Ser Met Lys
            440                 445                 450 gac ctt gag tac ata gaa cag ctg aaa gag ttg ata caa aaa gaa gca    1447
Asp Leu Glu Tyr Ile Glu Gln Leu Lys Glu Leu Ile Gln Lys Glu Ala
        455                 460                 465 ata cca gca cct tct ccc ata gag cag cgt tgg aca ggc cga agt aag    1495
Ile Pro Ala Pro Ser Pro Ile Glu Gln Arg Trp Thr Gly Arg Ser Lys
    470                 475                 480 agc cct atg agt cct gca ttc agc act gca gag gag gac att ttc tca    1543
Ser Pro Met Ser Pro Ala Phe Ser Thr Ala Glu Glu Asp Ile Phe Ser
485                 490                 495                 500 tgg gtt ggt ata atc atg tat ctc ccg aca gca gac cct cgc cag aga    1591
Trp Val Gly Ile Ile Met Tyr Leu Pro Thr Ala Asp Pro Arg Gln Arg
                505                 510                 515 aag gac atc acg gat gaa ttt ttc cac tat aga cat ttg aca cag gca    1639
Lys Asp Ile Thr Asp Glu Phe Phe His Tyr Arg His Leu Thr Gln Ala
            520                 525                 530 aaa ttg tgg gac cag tat tct gcg tat gaa cat tgg gct aaa att gag    1687
Lys Leu Trp Asp Gln Tyr Ser Ala Tyr Glu His Trp Ala Lys Ile Glu
        535                 540                 545 ata cca aag gat aaa gag gaa ctt gaa gcc cta caa gaa aga ctc aga    1735
Ile Pro Lys Asp Lys Glu Glu Leu Glu Ala Leu Gln Glu Arg Leu Arg
    550                 555                 560 aaa cga ttc ccg gtg gat gca tac aac aaa gca cga agg gag ctg gac    1783
Lys Arg Phe Pro Val Asp Ala Tyr Asn Lys Ala Arg Arg Glu Leu Asp
565                 570                 575                 580 cca aac aga att ctc tca aac aac atg gtg gaa aag ctc ttc cct gtc    1831
Pro Asn Arg Ile Leu Ser Asn Asn Met Val Glu Lys Leu Phe Pro Val
                585                 590                 595 tcc aag act gct taa aaacatttc atcaatagtt tttttgctcc ttgaagtacc    1886
Ser Lys Thr Ala  *
            600 acttttggaa tcctataacg ttgcatctac aagtgtttgt aagaagagtg aagccgatat    1946
```

```
attggtcaca aaaaaagttt acattgagtt ttactactat ttttttttc gcagttcccc    2006 tgaataaata tacttgttgt tctattcc                                      2034
```

<210> SEQ ID NO 13
<211> LENGTH: 600
<212> TYPE: PRT
<213> ORGANISM: Brassica oleracea

<400> SEQUENCE: 13

```
Met Leu Arg Ser Leu Leu Arg Arg Ser Asn Ala Arg Ser Leu Arg
 1               5                  10                  15

Pro Pro Phe Pro Pro Leu Arg Thr Leu Cys Thr Ser Gly Gln Thr Leu
            20                  25                  30

Thr Pro Ala Pro Pro Pro Pro Pro Pro Pro Pro Ile Ser Ser
            35                  40                  45

Ser Ala Ser Glu Lys Glu Phe Arg Lys Tyr Ala Gly Tyr Ala Ala Leu
 50                  55                  60

Ala Leu Phe Ser Gly Ala Ala Thr Tyr Phe Ser Phe Pro Phe Pro Glu
65                  70                  75                  80

Asn Ala Lys His Lys Lys Ala Gln Ile Phe Arg Tyr Ala Pro Leu Pro
                85                  90                  95

Glu Asp Leu His Thr Val Ser Asn Trp Ser Gly Thr His Glu Val Gln
                100                 105                 110

Thr Arg Asn Phe Asn Gln Pro Gly Thr Leu Ala Asp Leu Glu Ala Leu
            115                 120                 125

Val Lys Glu Ala His Glu Lys Lys Asn Arg Ile Arg Pro Val Gly Ser
130                 135                 140

Gly Leu Ser Pro Asn Gly Ile Gly Leu Ser Arg Ser Gly Met Val Asn
145                 150                 155                 160

Leu Ala Leu Met Asp Lys Val Leu Glu Val Asp Lys Glu Lys Lys Arg
                165                 170                 175

Val Arg Val Gln Ala Gly Ile Arg Val Gln Gln Leu Val Asp Ala Ile
            180                 185                 190

Gln Glu Tyr Gly Leu Thr Leu Gln Asn Phe Ala Ser Ile Arg Glu Gln
        195                 200                 205

Gln Ile Gly Gly Ile Ile Gln Val Gly Ala His Gly Thr Gly Ala Arg
    210                 215                 220

Leu Pro Pro Ile Asp Glu Gln Val Ile Gly Met Lys Leu Val Thr Pro
225                 230                 235                 240

Ala Lys Gly Thr Ile Glu Leu Ser Lys Asp Asn Asp Pro Glu Leu Phe
                245                 250                 255

His Leu Ala Arg Cys Gly Leu Gly Gly Leu Gly Val Val Ala Glu Val
            260                 265                 270

Thr Leu Gln Cys Val Glu Arg Gln Glu Leu Glu His Thr Tyr Val
        275                 280                 285

Ser Thr Leu Glu Glu Ile Lys Lys Asn His Lys Lys Leu Leu Ser Thr
    290                 295                 300

Asn Lys His Val Lys Tyr Leu Tyr Ile Pro Tyr Thr Asp Thr Val Val
305                 310                 315                 320

Val Val Thr Cys Asn Pro Val Ser Lys Trp Ser Gly Ala Pro Lys Asp
                325                 330                 335

Lys Pro Lys Tyr Thr Thr Glu Gly Ala Leu Lys His Val Arg Asp Leu
            340                 345                 350
```

-continued

Tyr Arg Glu Ser Ile Val Lys Tyr Arg Val Gln Asp Ser Ser Lys Lys
        355                 360                 365

Thr Pro Asp Ser Arg Glu Pro Asp Ile Asn Glu Leu Ser Phe Thr Glu
    370                 375                 380

Leu Arg Asp Lys Leu Ile Ala Leu Asp Pro Leu Asn Asp Val His Val
385                 390                 395                 400

Gly Lys Val Asn Gln Ala Glu Ala Glu Phe Trp Lys Lys Ser Glu Gly
                405                 410                 415

Tyr Arg Val Gly Trp Ser Asp Glu Ile Leu Gly Phe Asp Cys Gly Gly
            420                 425                 430

Gln Gln Trp Val Ser Glu Thr Cys Phe Pro Ala Gly Thr Leu Ala Lys
        435                 440                 445

Pro Ser Met Lys Asp Leu Glu Tyr Ile Glu Gln Leu Lys Glu Leu Ile
    450                 455                 460

Gln Lys Glu Ala Ile Pro Ala Pro Ser Pro Ile Glu Gln Arg Trp Thr
465                 470                 475                 480

Gly Arg Ser Lys Ser Pro Met Ser Pro Ala Phe Ser Thr Ala Glu Glu
                485                 490                 495

Asp Ile Phe Ser Trp Val Gly Ile Ile Met Tyr Leu Pro Thr Ala Asp
            500                 505                 510

Pro Arg Gln Arg Lys Asp Ile Thr Asp Glu Phe His Tyr Arg His
        515                 520                 525

Leu Thr Gln Ala Lys Leu Trp Asp Gln Tyr Ser Ala Tyr Glu His Trp
    530                 535                 540

Ala Lys Ile Glu Ile Pro Lys Asp Lys Glu Glu Leu Glu Ala Leu Gln
545                 550                 555                 560

Glu Arg Leu Arg Lys Arg Phe Pro Val Asp Ala Tyr Asn Lys Ala Arg
                565                 570                 575

Arg Glu Leu Asp Pro Asn Arg Ile Leu Ser Asn Asn Met Val Glu Lys
            580                 585                 590

Leu Phe Pro Val Ser Lys Thr Ala
        595                 600

<210> SEQ ID NO 14
<211> LENGTH: 3120
<212> TYPE: DNA
<213> ORGANISM: Arabidopsis thaliana
<220> FEATURE:
<221> NAME/KEY: exon
<222> LOCATION: (260)...(937)
<221> NAME/KEY: exon
<222> LOCATION: (1053)...(1319)
<221> NAME/KEY: exon
<222> LOCATION: (1602)...(1787)
<221> NAME/KEY: exon
<222> LOCATION: (1877)...(2302)
<221> NAME/KEY: exon
<222> LOCATION: (2634)...(2777)
<221> NAME/KEY: exon
<222> LOCATION: (3026)...(3103)

<400> SEQUENCE: 14
accgttcgac ccgattctca tgcgggacag aaaaccaaaa ggcccaaaac tacaagtcta    60
caataaaatt tctggttttg tttggttttt gaatgtggac aaactagtta ccaatttgtt   120
cattaacaaa ttactcggct caaattatga aaacagaaat aaaatcaggg tataatggaa   180
actttcttaa atcactaaac ccgatcctgt acaagaacat ttccctcagg ttcagatcgc   240
ctgaagttaa acaaaaaaaa tgctccggtc acttcttctc cgacgctccg tcggccattc   300

-continued

```
tctcggaacc ctatctccgt cttcatccac catccgttcc tcattttcgc ctcatcgtac      360
tctctgcacc accggtcaaa cattgacacc accaccgccg ccaccgccac gtcctccacc      420
tccgcctccg gccaccgcct cagaagctca attccgtaaa tacgccggat acgcagcact      480
cgctatcttc tctggagttg ctacctattt ctcatttcca ttccctgaga atgctaaaca      540
caagaaggct caaatcttcc gttacgctcc tttacctgaa gatcttcaca ctgtctctaa      600
ttggagtggt actcatgagg tacagactag gaactttaat caaccggaga atcttgctga      660
tctcgaagct cttgttaagg aatctcatga agaagtta aggattcgtc ccgttggatc        720
gggtctctcg cctaatggga ttggtttgtc tcgctctggg atggtgaatc tggcgcttat      780
ggataaagtt ctagaggtgg ataaagagaa gaagagagtt acggtgcagg ctgggattag      840
ggtccagcaa ttggttgacg ccattaaaga ctatggtctt actcttcaga actttgcctc      900
cattagagag cagcagattg gtggtattat tcaggtttgc atatgtttct ctcccttgtg      960
tgaagtctag ggttgtgaaa ctaatggaga atctgaaaca attttagttg ttcgtctttta    1020 tcttgtgctt tgaggttttt agagtctata tttttgttta cgttcaggtt ggggcacatg     1080
ggacaggtgc tagattgcct cctattgatg agcaggtgat cagtatgaag ctggttactc     1140
ctgcgaaggg aacaattgaa ctttcaagag agaaagatcc ggagctcttt catctagctc     1200
gatgtggcct tggtggactt ggagttgttg ctgaggtcac cctccaatgc gttgcaagac     1260
atgaacttgt ggaacacaca tacgtctcaa acttgcaaga aatcaagaaa atcacaagt     1320 taagtatcgc taactttcgc tatattagtc tccatattat ggctccagct tagaaaatca    1380
tgctcagtat acgacttttc ttctggtcag attatcagag aagtatcaga ttgatgcaag    1440
agcttaaagt ttttttcact ttttagtact gcccatatca tttggcatag tgcattctag    1500
catttgggaa atcactccct ctactttgaa gcaaattgat cccataaatt ggctcagggt    1560
ggaacgtttc ctaacttttg ttttgtttct ggctgttcag aaaattgctc tctgcaaaca    1620
agcatgttaa gtacctatat attccttata ccgacacagt cgtggttgta acatgcaatc    1680
ctgtatcaaa atggagtggg ccacctaagg acaaaccaaa gtacactaca gatgaggctg    1740
tacagcatgt ccgtgatctc tacagagaga gcattgtgaa gtataggtat cgttatgctt    1800
aagtcttatg tgtaacttga tttctctaat gtggaggact gaatgaaatg caaataatt     1860 ttttactatg atgtataggg tccaggactc tggtaagaag tctcctgaca gcagtgagcc    1920
agacatacag gagctttcat ttacagagtt gagagacaaa ctacttgccc ttgatcctct    1980
caatgacgtt cacgttgcaa agtaaatcaa gctgaggcag agttttggaa aaaatcagaa    2040
ggatatagag tagggtggag tgatgaaatt ctgggctttg actgtggtgg tcagcagtgg    2100
gtgtcagaat cttgtttttcc tgctggaacc ctcgccaacc ctagcatgaa agaccttgaa    2160
tacatagaag agctgaaaaa actaatagaa aaggaagcaa taccagcacc tgctccaata    2220
gagcagcgat ggacagctcg aagtaagagc cccattagtc ctgcattcag cacttcagag    2280
gatgatattt tctcatgggt aactcttgtt ttatgtcgtt tatccttcca tttacttctc    2340
tttgactttc atgaaagtat gaagagatat tggtgtcaat ctataggaag cttgttttgt    2400
ggctctgcct ttgtggtgga ggaaaacatg tgatatattg atgttaaaat gttcatagac    2460
aaagaagaaa ccgtaaaaat gatgttacat actgtactct taggtgctgg attgttgttt    2520
cacttggtag attttgttg ttggccaacc ttgttccaac accgactgtt tgcctttttt      2580
ctctttcaaa tgctagtcat ctacagttat aatatgctac attacatttg tctcaggttg    2640
gtataatcat gtacctcccg acagcagacc ctcgccagag aaaggacatc acagatgaat    2700
```

-continued

```
ttttccacta tagacatttg acacagaaac aattgtggga tcaattttct gcgtatgaac    2760
attgggctaa aattgaggta atcgtagatt ttctaatcta aatatgagat tcttgtatct    2820
taacacacag ataccatcat tctcacttaa ctatgtcctt ctgattcact cacaaaaagt    2880
ctctgtatct taattacatt ttttctgctt gaactacaac tgtcctcatt gtgagaagta    2940
agcaaaggga atgagaatct gttgaggtaa ctatttagag tgtagacaat ttctaatgtt    3000
ttctgtttga tatttatata atcagatacc aaaagacaaa gaagaacttg aagccttaca    3060
ggcaagaata agaaaacgtt tcccagtgga tgcatacaac aaattcctag gatcctcgag    3120
```

<210> SEQ ID NO 15
<211> LENGTH: 592
<212> TYPE: PRT
<213> ORGANISM: Arabidopsis thaliana

<400> SEQUENCE: 15

```
Met Leu Arg Ser Leu Leu Arg Arg Ser Val Gly His Ser Leu Gly
 1               5                  10                  15

Thr Leu Ser Pro Ser Ser Thr Ile Arg Ser Phe Ser Pro His
            20                  25                  30

Arg Thr Leu Cys Thr Thr Gly Gln Thr Leu Thr Pro Pro Pro Pro
         35                  40                  45

Pro Pro Arg Pro Pro Pro Pro Pro Ala Thr Ala Ser Glu Ala Gln
 50                  55                  60

Phe Arg Lys Tyr Ala Gly Tyr Ala Ala Leu Ala Ile Phe Ser Gly Val
 65                  70                  75                  80

Ala Thr Tyr Phe Ser Phe Pro Phe Pro Glu Asn Ala Lys His Lys Lys
                 85                  90                  95

Ala Gln Ile Phe Arg Tyr Ala Pro Leu Pro Glu Asp Leu His Thr Val
            100                 105                 110

Ser Asn Trp Ser Gly Thr His Glu Val Gln Thr Arg Asn Phe Asn Gln
         115                 120                 125

Pro Glu Asn Leu Ala Asp Leu Glu Ala Leu Val Lys Glu Ser His Glu
     130                 135                 140

Lys Lys Leu Arg Ile Arg Pro Val Gly Ser Gly Leu Ser Pro Asn Gly
145                 150                 155                 160

Ile Gly Leu Ser Arg Ser Gly Met Val Asn Leu Ala Leu Met Asp Lys
                 165                 170                 175

Val Leu Glu Val Asp Lys Glu Lys Arg Val Thr Val Gln Ala Gly
            180                 185                 190

Ile Arg Val Gln Gln Leu Val Asp Ala Ile Lys Asp Tyr Gly Leu Thr
         195                 200                 205

Leu Gln Asn Phe Ala Ser Ile Arg Glu Gln Gln Ile Gly Gly Ile Ile
     210                 215                 220

Gln Val Phe Val Tyr Val Gln Val Gly Ala His Gly Thr Gly Ala Arg
225                 230                 235                 240

Leu Pro Pro Ile Asp Glu Gln Val Ile Ser Met Lys Leu Val Thr Pro
                 245                 250                 255

Ala Lys Gly Thr Ile Glu Leu Ser Arg Glu Lys Asp Pro Glu Leu Phe
            260                 265                 270

His Leu Ala Arg Cys Gly Leu Gly Gly Leu Gly Val Val Ala Glu Val
         275                 280                 285

Thr Leu Gln Cys Val Ala Arg His Glu Leu Val Glu His Thr Tyr Val
     290                 295                 300
```

```
Ser Asn Leu Gln Glu Ile Lys Lys Asn His Lys Lys Leu Leu Ser Ala
305                 310                 315                 320

Asn Lys His Val Lys Tyr Leu Tyr Ile Pro Tyr Thr Asp Thr Val Val
            325                 330                 335

Val Val Thr Cys Asn Pro Val Ser Lys Trp Ser Gly Pro Pro Lys Asp
            340                 345                 350

Lys Pro Lys Tyr Thr Thr Asp Glu Ala Val Gln His Val Arg Asp Leu
        355                 360                 365

Tyr Arg Glu Ser Ile Val Lys Tyr Arg Arg Val Gln Asp Ser Gly Lys
    370                 375                 380

Lys Ser Pro Asp Ser Ser Glu Pro Asp Ile Gln Glu Leu Ser Phe Thr
385                 390                 395                 400

Glu Leu Arg Asp Lys Leu Leu Ala Leu Asp Pro Leu Asn Asp Val His
                405                 410                 415

Val Gly Lys Val Asn Gln Ala Glu Ala Glu Phe Trp Lys Lys Ser Glu
                420                 425                 430

Gly Tyr Arg Val Gly Trp Ser Asp Glu Ile Leu Gly Phe Asp Cys Gly
        435                 440                 445

Gly Gln Gln Trp Val Ser Glu Ser Cys Phe Pro Ala Gly Thr Leu Ala
    450                 455                 460

Asn Pro Ser Met Lys Asp Leu Glu Tyr Ile Glu Glu Leu Lys Lys Leu
465                 470                 475                 480

Ile Glu Lys Glu Ala Ile Pro Ala Pro Ala Pro Ile Glu Gln Arg Trp
                485                 490                 495

Thr Ala Arg Ser Lys Ser Pro Ile Ser Pro Ala Phe Ser Thr Ser Glu
            500                 505                 510

Asp Asp Ile Phe Ser Trp Val Val Gly Ile Ile Met Tyr Leu Pro Thr
            515                 520                 525

Ala Asp Pro Arg Gln Arg Lys Asp Ile Thr Asp Glu Phe Phe His Tyr
        530                 535                 540

Arg His Leu Thr Gln Lys Gln Leu Trp Asp Gln Phe Ser Ala Tyr Glu
545                 550                 555                 560

His Trp Ala Lys Ile Glu Ile Pro Lys Asp Lys Glu Glu Leu Glu Ala
            565                 570                 575

Leu Gln Ala Arg Ile Arg Lys Arg Phe Pro Val Asp Ala Tyr Asn Lys
            580                 585                 590
```

PRODUCTION OF ASCORBIC ACID IN PLANTS

This is the U.S. National Phase under 35 U.S.C. 371 of International Application PCT/EP98/02830, filed May 7, 1998.

FIELD OF THE INVENTION

The present invention relates to a polynucleotide, in particular a cDNA, which codes for L-galactono-γ-lactone dehydrogenase (GLDase), an enzyme involved in the biosynthesis of ascorbic acid (vitamin C) in plants. The invention further relates to the use of this cDNA for the synthesis of the enzyme and for the production of transgenic plant and animal cells, plant tissues and plants producing the enzyme.

BACKGROUND OF THE INVENTION

Ascorbic acid is synthesized in all higher plants and in almost all higher animals, with the exception of humans and other primates, the guinea pig and a number of birds. Opinions differ concerning the presence of ascorbic acid in micro-organisms. It appears to be present in a number of yeasts, although there are also reports which suggest that ascorbic acid analogues are found in micro-organisms.

In the animal and plant kingdom, ascorbic acid is formed by different routes. In animals, glucose is the primary precursor for the biosynthesis of ascorbic acid, and the last step in the biosynthetic pathway is catalyzed by a microsomal enzyme: L-gulono-γ-lactone oxidase. This enzyme has already been isolated from rat, goat and chicken liver and kidney tissues.

The pathway of ascorbic acid biosynthesis in plants, however, is not yet entirely clear, but there are indications that at least two different biosynthetic pathways exist. Isherwood et al., Biochem. J. 56:1–15 (1954) postulated that the biosynthesis of ascorbic acid starting from D-galactose proceeds via L-galactono-γ-lactone to L-ascorbic acid. Mapson et al., Biochem. J. 56:21–28 (1954) were the first to study this oxidation of L-galactono-γ-lactone to ascorbic acid, a reaction which is catalyzed by L-galactono-γ-lactone dehydrogenase.

The presence of L-galactono-γ-lactone dehydrogenase activity has been described for different plants, including pea, cabbage and potato. Ôba et al., J. Biochem. 117:120–124 (1995) have recently purified the enzyme activity from sweet potato tubers.

Distinct from this biosynthetic pathway, however, an alternative pathway has been proposed which takes as starting point the conversion of D-glucose, and proceeds via L-glucosone and L-sorbosone to ascorbic acid. An NADP-dependent dehydrogenase, which catalyses the conversion of L-sorbosone to ascorbic acid, has been partially purified from bean and spinach leaves (Loewees et al., Plant Physiol. 94:1492–1495 (1990)).

The primary function of ascorbate is as a reducing agent. This is universal. Ascorbic acid is also important as a cofactor for certain enzymatic reactions, including the production of collagen in vertebrates. Since humans are completely dependent on ingested food for the acquisition of ascorbate, it is desirable to increase the vitamin C content of plants and fruit.

Owing to its reducing activity, vitamin C plays a role in the protection of plants and animals against environmental stresses including heat, cold, drought, oxidative stress etcetera. Less stress-sensitive or even stress-resistant plants can therefore play an important part in the economy and agriculture of the world.

BRIEF SUMMARY OF THE INVENTION

It is the object of the present invention to create the possibility of genetically modifying plants such that they contain an increased content of ascorbic acid relative to non-modified plants.

For this purpose the invention provides a polynucleotide in isolated form, which polynucleotide codes for a protein with the activity of the enzyme L-galactono-γ-lactone dehydrogenase, which polynucleotide comprises at least the L-galactono-γ-lactone dehydrogenase activity-determining parts of the coding part of the nucleotide sequence, which is shown in FIG. 3, or a sequence derived therefrom on the basis of the degeneration of the genetic code. The invention is of course not limited to polynucleotides with exactly the same sequence as that shown in FIG. 3. It will be apparent to the molecular biologist skilled in the techniques that a certain degree of modification of the sequence shown in FIG. 3 is permitted while still falling within the scope of the claim. The polynucleotide is for instance the cDNA shown in FIG. 3.

Polynucleotides according to the invention can be used in the production of transgenic plant and animal cells, plant tissues or plants with an increased content of the enzyme L-galactono-γ-lactone dehydrogenase relative to non-transgenic plant cells, plant tissues or plants. Such an increased concentration of GLDase will result in plant cells, plant tissues or plants with an increased content of ascorbic acid and with an increased capacity for biosynthesis relative to non-transgenic plant cells, plant tissues or plants.

Plants which can advantageously be used for transformation with the polynucleotide according to the invention are for instance thale cress (*Arabidopsis thaliana*), tobacco (*Nicotiana tabacum*), tomato, potato, or corn, without this list being limitative.

Polynucleotides according to the invention can likewise be expressed in eukaryotic cells, such as yeast cells or mammalian cells, in particular fibrosarcoma cells.

The invention further relates to a recombinant L-galactono-γ-lactone dehydrogenase which can be obtained by expression of a polynucleotide according to the invention in a suitable host. The recombinant L-galactono-γ-lactone dehydrogenase can be isolated from transgenic plant tissues or transgenic plants, but also from yeasts or from animal cells.

The invention also relates to a transformation system, comprising a transformation vector or set of vectors, at least one of which includes a nucleotide sequence which codes for the enzyme L-galactono-γ-lactone dehydrogenase The transformation system preferably comprises Agrobacterium and a binary vector.

Plants or plant tissues with an increased ascorbic acid content can be produced by transforming a plant cell with a gene construct comprising at least the polynucleotide specified in the invention, optionally linked to targeting sequences for specific organelles, and/or in the presence of suitable transcription and/or translation regulation factors, and regenerating from the plant cell a transgenic plant or plant tissue. The gene construct with the polynucleotide according to the invention can optionally be combined with other genes coding for enzymes which can interfere in the ascorbic acid synthesis, such as L-sorbosone dehydrogenase, UDP-glucuronic acid epimerase, D-galacturonic acid dehydrogenase and ascorbateregulating enzymes, which may determine the rate of ascorbic acid synthesis The enzyme may ultimately be targeted to a particular part of the plant cell, such as the cytoplasm, vacuoles, chloroplasts, mitochondria, lysosomes, endoplasmatic reticulum, Golgi apparatus.

Eukaryotic cells expressing the enzyme GLDase can be obtained by transfection with the polynucleotide according to the invention.

Finally, the invention relates to a new method for purifying the enzyme L-galactono-γ-lactone dehydrogenase. This method comprises of passing a protein extract of cauliflower florets through an ion exchange column: collecting a number fractions eluting from the column and determining the GLDase activity of the fractions; combining fractions with GLDase activity and passing thereof through a Phenyl Sepharose CL 4B column; collecting the column eluate in a number of fractions and determining the GLDase activity of the fractions; combining those fractions with GLDase activity and passing thereof through a gel filtration column; collecting a number of fractions eluting from the column and determining the GLDase activity of the fractions; combining the fractions with GLDase activity and passing through an FPLC Resource Q-column; collecting a number of fractions eluting from the column and determining the GLDase activity of the fractions; combining the fractions with GLDase activity and passing thereof over an FPLC Poros 20 SP-column; collecting a number of fractions eluting from the column and determining the GLDase activity of the fractions. The enzyme purified by us is lycorine-insensitive, in contrast to the literature which states that L-galactono-γ-lactone dehydrogenase is inhibited by lycorine (De Tullio et al., Boll. Soc. Ital. Biol. Sper. 70:57–62 (1994); Arrigoni et al., Boll. Soc. Ital. Biol. Sper. 72:37–43 (1996))

Furthermore, the invention provides for a method for increasing the L-ascorbic acid levels in plants, comprising:
  a) provision of plants that have been transformed with the sense version of the GLDase gene, and
  b) providing the said plants with the precursor L-galactono-γ-lactone in order to induce increased L-ascorbic acid synthesis.

According to another aspect thereof the invention provides transgenic plants having in their genome an antisense version of the GLDase gene resulting in a decreased amount of ascorbic acid as compared to non-transgenic plants for use a model system or biosensor for oxidative stress.

The present invention will be elucidated with reference to the non-limitative examples provided below.

BRIEF DESCRIPTION OF THE DRAWINGS

FIG. 3 is the derived L-galactono-γ-lactone dehydrogenase amino acid sequence of the 1803 bp open reading frame (SEQ ID NO:12) which codes for 600 amino acids (SEQ ID NO:13).

FIG. 5 is the nucleotide (SEQ ID NO:14) and amino acid (SEQ ID NO:15) sequence of the genomic L-galactono-γ-lactone dehydrogenase clone from Arabidopsis.

DESCRIPTION OF THE PREFERRED EMBODIMENTS

EXAMPLES

Example 1

Purification of L-galactono-γ-lactone Dehydrogenase

1. Introduction

Figure 1:
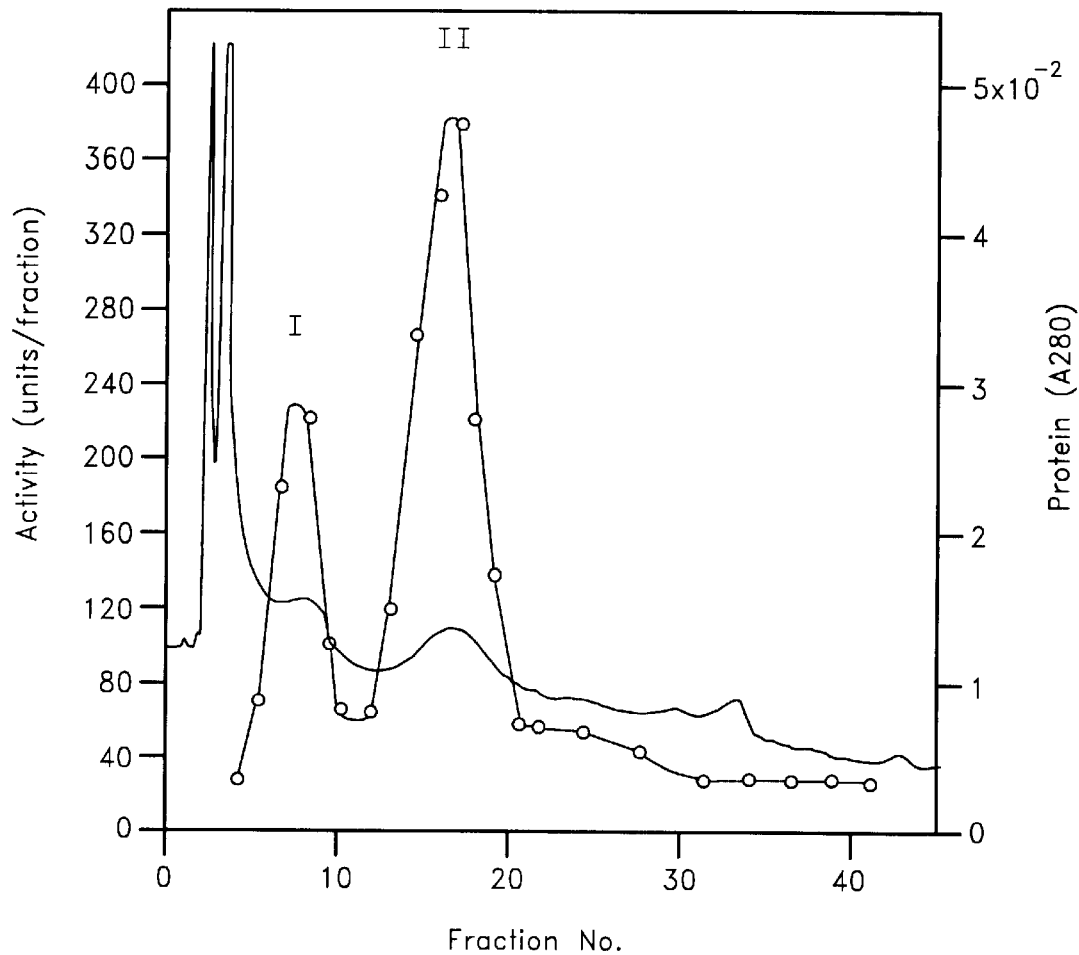
FIG. 1 is a graph of activity and protein concentrations of L-galactono-γ-lactone dehydrogenase in fractions eluted from a Poros 20 SP column.

Using a 5-step purification method which has not previously been described, an acceptable yield of the enzyme L-galactono-γ-lactone dehydrogenase (further designated GLDase) was obtained.

2. Materials and Methods 2.1. Materials

Sephacryl SF-200, DEAE Sepharose and Phenyl Sepharose CL-4B were obtained from Pharmacia, Sweden. L-galactono-γ-lactone, D-galactono-γ-lactone, D-gulono-γ-lactone, L-gulono-γ-lactone, L-mannono-γ-lactone, D-galactonic acid, D-glucuronic acid, D-gluconic acid and P-hydroxymercuribenzoic acid were from Sigma Chemical, USA. D-erythronic lactone, D-xylonic lactone and N-ethylmaleimide were purchased from Aldrich Chemical Company, USA. Restriction enzymes were from Pharmacia, Sweden and ($\alpha$-$^{32}$P)dCTP was from Amersham Corp., USA. The cauliflowers (*Brassica olecera* var. *botrytis*) were obtained from a field near Ghent and stored at 4° C. until use.

2.2. Preparation of an Extract

Cauliflower florets (7.5 kg) were cut into small pieces, weighed and homogenized in a pre-cooled blender in ice-cold buffer A (400 mM sucrose, 100 mM sodium phosphate buffer, pH 7.4) (1 l/kg fresh weight). The homogenate was pressed through four layers of Miracloth tissue (Calbiochem-Novabiochem Corp., La Jolla, Calif., USA) and centrifuged for 45 minutes at 13,500×g in a GS3 rotor (Sorvall). The pellet containing the mitochondria (about 250 g material) was kept at −70° C. until use.

Before use the pellet was slowly defrosted in a microwave oven and resuspended in 1/10 vol. (750 ml) buffer A. Cold acetone (−20° C.) was added slowly while stirring (10× vol.). The mixture stood for 30 minutes at 4° C. The precipitated protein was collected by filtration through prefilter paper (A15, Millipore, Bedford, USA) and resuspended in 1/10 vol. buffer B (40 mM Tris-HCl, pH 9.0) followed by 5 hours of dialysis against 10 volumes buffer B. The denatured proteins were removed by centrifugation (10,000×g for 15 minutes). GLDase was purified from the supernatant, further designated as "protein extract", using the purification procedure described below.

All operations relating to preparation of the extract and enzyme purification were performed at 4° C. unless otherwise stated.

2.3. Enzyme Purification

The protein extract was placed on a DEAE Sepharose column (5×12 cm) equilibrated with buffer B. After washing with 4 volumes of buffer B at a flow rate of 60 ml per hour, the elution was carried out with 0.5 M NaCl in the same buffer. Fractions of 8 ml were collected at a flow rate of 60 ml per hour.

The GLDase activity of the fractions was is determined spectrophotometrically by monitoring the L-galactono-γ-lactone dehydrogenase-dependent reduction of cytochrome c at 22° C. A typical reaction mixture contained the enzyme extract, 1.5 mg/ml cytochrome c and 4.2 mM L-galactono-γ-lactone in 0.05 M Tris-HCl buffer (pH 8.4). Reduction of cytochrome c was monitored by determining the absorption increase at 550 nm. Under these conditions the speed of the reaction was linear in respect of time for an initial period of 15 minutes. One unit of enzyme activity was defined as the quantity of enzyme reducing 2 μmol of cytochrome C per minute.

The fractions containing GLDase activity were pooled and ammonium sulphate was added up to a concentration of 1 M. Hereafter the extract was loaded onto a Phenyl Sepharose CL 4B column (2.2×15.0 cm) which was equilibrated with buffer C (1 M ammonium sulphate, 25 mM sodium phosphate, pH 7.0). After washing with two volumes of buffer C the elution was carried out with a linear gradient of 0–80% ethylene glycol in 25 mM sodium phosphate, pH 7.0, at a flow rate of 30 ml/hour.

The GLDase activity of the fractions was again determined and GLDase-containing fractions were collected, concentrated to 10 ml by ultrafiltration using a PM 10 membrane (Amicon Corp.) and loaded onto a Sephacryl SF-200 gel filtration column (2.6×94 cm) equilibrated in buffer D (20% ethylene glycol, 40 mM NaCl, 80 mM sodium phosphate, pH 7.4). The enzyme was eluted with the same buffer at a flow rate of 25 ml per hour. Fractions of 5 ml were collected and fractions containing activity were combined. It was possible to keep the gel filtration preparation at 4° C. for several weeks without loss of activity.

Two gel filtration preparations were pooled. The preparations were concentrated and the buffer was replaced by buffer E (20% ethylene glycol, 20 mM Tris-HCl, pH 8.0) by means of ultrafiltration. The resulting enzyme solution was loaded onto a 6 ml Resource Q column (Pharmacia) which was equilibrated beforehand with buffer E and coupled to an FPLC system (Pharmacia). The flow rate was 1 ml per minute. Elution was carried out with a gradient of 0 to 450 mM NaCl as follows: 0 to 85 mM in 18 minutes, 85 to 110 mM in 10 minutes, 110 to 130 mM in 14 minutes and 130 to 450 mM in 10 minutes. Fractions of 1 ml were collected. The activity of the main peak, which eluted at 120 mM NaCl, was pooled and brought to pH 6 with 50 mM sodium phosphate.

The pooled fractions were loaded onto a Poros 20 SP column (Pharmacia) coupled to an FPLC and equilibrated in buffer F (20 mM sodium phosphate, pH 6.0, 20% ethylene glycol) at a flow rate of 1 ml/minute. The elution was carried out with a gradient of 0 to 500 mM NaCl in buffer F as follows: 125 to 225 mM in 40 minutes and 225 to 500 mM in 37 minutes. Fractions of 2 ml were collected. Two peaks with activity eluted: peak I at 210 mM and peak II at 225 mM NaCl. Peak II was dialyzed against 10 mM sodium phosphate, pH 7.2.

A Zorbax gel filtration column (9.4×250 mm, Zorbax Bioseries GF-250) coupled to an HPLC and equilibrated in 750 mM NaCl, 50 mM sodium phosphate, pH 7.2 was used as final purification step.

Figure 2:
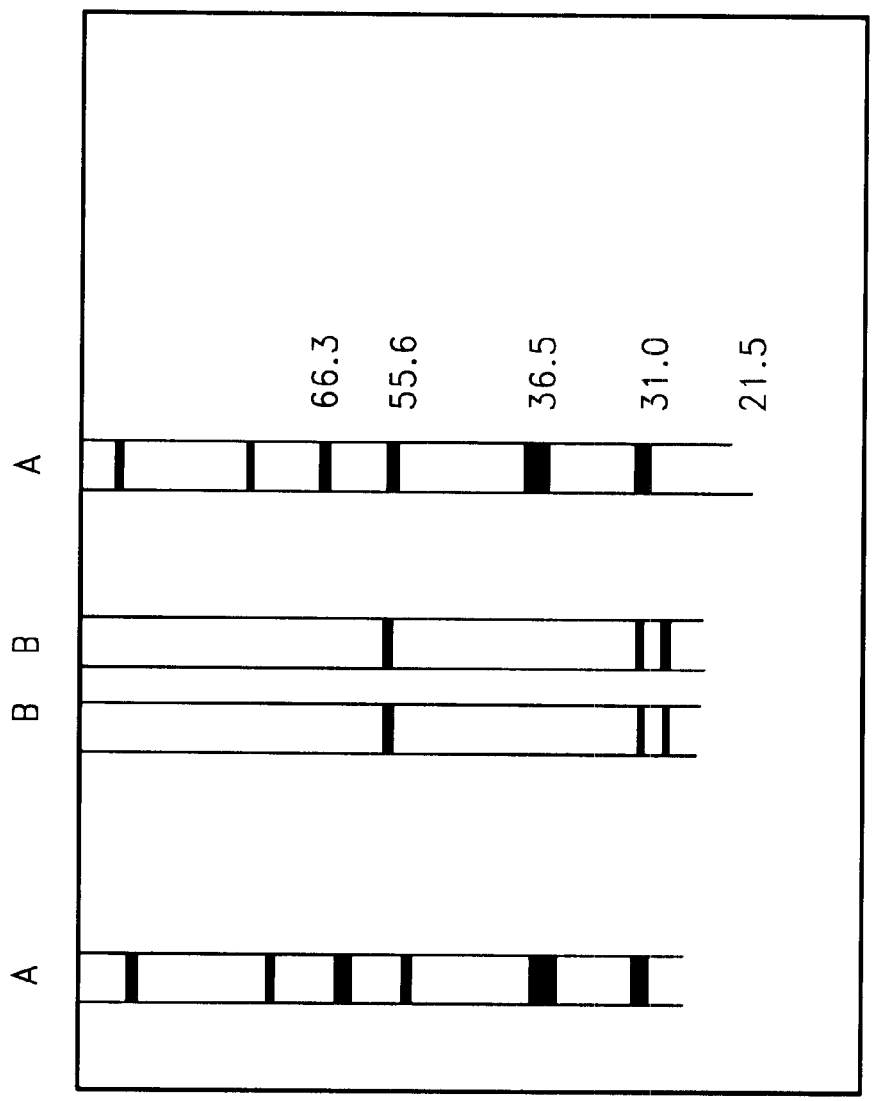
FIG. 2 is an SDS PAGE of purified L-galactono-γ-lactone dehydrogenase.

Table 1 shows a summary of the purification of GLDase from cauliflower florets. Because the enzymatic activity was most stable in 20% ethylene glycol, this reagent was included in all buffers except the buffers which were used in the first purifications steps with the DEAE Sepharose and Phenyl Sepharose chromatography. After the DEAE Sepharose step the total GLDase activity increased slightly, probably due to removal of inhibitory compounds which were present in the original crude extract. The FPLC Resource step increased the purification factor from 63 to 900, although the recovery is only 42% in comparison with the activity present in the gel-filtered pool. By the subsequent Poros 20 SP column the activity was separated into two peaks, designated I and II in FIG. 1. The activity from the latter peak was used for further analysis. Table 1 shows that GLDase was 1693 times more purified from the mitochondrial fraction with a recovery of 1.1%. The purity of the enzyme was tested by means of analytical SDS polyacrylamide gel electrophoresis (SDS PAGE) in slab gels of 10% polyacrylamide as according to Chua, Methods Enzymol. 69:434–446 (1980). Proteins were visualized either by means of Coomassie Brilliant Blue R250 staining (Chua (1980), supra) or silver nitrate staining (Merril et al., Methods Enzymol. 104:441–447 (1984)). Three polypeptide bands were found with molecular masses of about 56 kDa, 30 kDa and 26 kDa (see FIG. 2).

A partial amino acid sequence was determined as follows. Purified GLDase from the Porous 20 SP purification step was separated by means of SDS-PAGE. The proteins were blotted onto polyvinylidene difluoride (PVDF) membranes (Millipore, Bedford, USA) as described by Bauw et al., Proc. Natl. Acad. Sci. USA 4806–4810 (1987) with 50 mM Tris/50 mM boric acid (pH 8.3) as transfer buffer. The transfer was carried out for at least 8 hours at 35 Volts with a Bio-Rad Transblot apparatus. PVDF membrane-bound polypeptides were visualized by staining with 0.1% Amido black solution. The polypeptide bands were excised and a trypsin digestion was performed in situ, followed by reversed phase HPLC separation of the generated peptides, as previously described by Bauw et al., Proc. Natl. Acad. Sci. USA 86:7701–7705 (1989). Partial amino acid sequence determination by Edman degradation was carried out on an Applied Biosystems model 473A protein sequencer in accordance with the instructions of the manufacturer.

Table 2 shows the sequences of a number of peptides derived from the GLDase. This shows inter alia that the two low-molecular bands are dissociation products of the 56 kDa band. The $NH_2$ terminal sequences of the 56 kDa and the 30 kDa polypeptide bands are identical.

Example 2

Sensitivity to Lycorine

The literature states that lycorine, a pyrrole phenanthridine alkaloid present in different plants of the Amaryllidaceae, inhibits the ascorbic acid synthesis at concentrations from 1 μM. It has recently been demonstrated that the inhibition of lycorine is based on an interaction with the enzyme L-galactono-γ-lactone dehydrogenase (De Tullio et al., (1994), supra; Arrigoni et al., (1996), supra).

Lycorine was isolated from the plant *Crinum asiaticum* and the identity of the isolated product was verified by NMR, electron spray mass spectrometry HPLC analysis and capillary electrophoresis. Fractions of L-galactono-γ-lactone dehydrogenase activity isolated from the gel filtration column were tested for their activity in two different buffers in the presence of 5 or 50 μM lycorine (see table 3).

All data indicate that the isolated GLDase is insensitive to the inhibitor up to a concentration of 50 μM. Additional tests did not show a decrease in activity even in 100 μM lycorine.

A pre-incubation of one hour of the enzyme with lycorine did not influence the enzyme activity.

TABLE 3

Activity of the enzyme expressed in increase in absorption at 550 nm/second

| Concentration lycorine (µM) | 0 | 5 | 50 |
|---|---|---|---|
| 75 mM PO4 pH 8 | 1.882 | 1.690 | 1.768 |
| 75 mM PO4 pH 7.5 | 1.385 | 1.372 | 1.254 |
| 75 mM PO4 pH 7.0 | 0.980 | 0.857 | 0.842 |
| 75 mM Tris pH 8.9 | 5.438 | 5.199 | 5.507 |
| 75 mM Tris pH 8.2 | 6.365 | 6.400 | 6.127 |
| 75 mM Tris pH 7.4 | 3.627 | 3.927 | 3.743 |

Example 3

Isolation of the cDNA 300 mg cauliflower florets were ground to a powder in liquid nitrogen with a pestle and mortar. The powder was suspended in 0.5 ml ice-cold extraction buffer (0.1 M LiCl, 5 mM EDTA, 1% (w/v) SDS and 0.2 M Tris-HCl, pH 7.5) and extracted twice more with phenol/$CH_3Cl$ alcohol (25:24:1). The aqueous phase was adjusted to a final concentration of 3 M LiCl and left on ice for 4 hours. The precipitate was collected by centrifuging for 10 minutes at 20,000×g and the pellet was washed with 1 ml 3 M LiCl and resuspended in 250 µl $H_2O$ treated with diethyl pyrocarbonate. The LiCl precipitate was repeated and the pellet washed and resuspended in 250 µl $H_2O$ treated with diethyl pyrocarbonate (DEPC). The suspension was centrifuged for 10 minutes at 20,000×g to remove insoluble material. Sodium acetate was added to an end concentration of 0.3 M followed by addition of 2 volumes ethanol and incubation for 15 minutes at −70° C. The precipitate was collected by centrifuging for minutes at 20,000×g.

The RNA pellet was washed with 70% ethanol and resuspended in 25 µl $H_2O$ treated with DEPC. The RNA isolated from cauliflower florets (4 µg) was used to synthesize the first strand of cDNA as specified in the instruction manual for Superscript™ Preamplification System for First Strand cDNA Synthesis of Gibco BRL.

Degenerated oligonucleotides corresponding with the partial amino acid sequences as shown in example 1 were designed and synthesized on an oligonucleotide synthesizer (Applied Biosystems, Poster City, Calif., USA) and used as primers in PCR reactions. The peptide sequences designated 1, 4 and 7 in table 2 were used to. design the corresponding coding and complementary oligonucleotides. First-strand cDNA synthesized from cauliflower florets was used as a template. The amplification mixture consisted of 130 ng matrix DNA, PCR buffer (100 mM Tris-HCl, 500 mM KCl, 1.5 mM $MgCl_2$, pH 8.3), 200–300 ng of each primer, 2.5 mM cNTP and 1 unit Taq polymerase in a total volume of 50 µl.

The amplification program consisted of 32 cycles of denaturation for 1 minute at 94° C., annealing for 1 minute at 50° C. and primer extension for 2 minutes at 72° C. The reaction products were separated on 1% agarose gels, excised and purified in accordance with the QIAEX handbook of Qiagen GmbH, Germany. The purified products were cloned into a pGEM-T vector (Promega, Wis., USA). Of the amplified 250 bp to 400 bp bands which were subcloned into a pGEM-T vector, a 250 bp fragment, which contained a nucleotide sequence corresponding to the amino acid sequence of one of the previously determined internal peptides, was radioactively labelled and used as probe to screen a cDNA library of cauliflower. The cDNA library was constructed in λZAP II (Stratagene, La Jolla, Calif., USA) and generously donated by Professor J. S. Hyams (University, London, UK). Portions of the cDNA library were plated using *Escherichia coli* XL-1 Blue-cells on 23×23 cm baking plates (Nunc, Roskilde, Denmark) with NZY agar. About 600,000 plaques from the library were transferred in duplicate to nylon membranes (HYbond $N^+$; Amersham Corp., USA). The membranes were treated in accordance with the instructions of the manufacturer for plaque blotting. DNA was fixed to the membranes by radiation with ultraviolet light (UV Stratalinker, Stratagene, La Jolla, Calif., USA). The membranes were subsequently incubated with the 250 bp PCR amplified fragment which was labelled with ($\alpha$-$^{32}$P)dCTP with a random primed DNA labelling kit from Boehringer Mannheim, Germany. The membranes were first washed for 4 hours at 65° C. in a hybridization buffer (1% (w/v) of bovine serum albumin, 7% (w/v) SDS, 1 mM EDTA and 0.25 M sodium phosphate, pH 7.2) followed by 20 hours of incubation with the $^{32}$P-labelled probe in the hybridization buffer at 65° C. The membranes were then rinsed twice for 15 minutes with 2×SSC containing and 1% SDS at room temperature and exposed to X-Omat AR-film (Kodak, Conn., USA).

Different positive clones were found. After in vivo excision of the Bluescript plasmid followed by digestion with EcoRI and KpnI the two longest cDNA inserts were found to be approximately 2000 bp long. Subcloning and sequence determination revealed an uninterrupted open reading frame of 1803 nucleotides. The open reading frame contained all the tryptic peptides which had previously been sequenced, the $NH_2$ terminal amino acid sequence, the first ATG codon (startcodon) (at position 56), and ended with a TAA terminator codon from which it was concluded that the full length cDNA corresponding to the purified protein had been isolated (SEQ. ID NO:12).

FIG. 3 shows the derived amino acid sequences of the 1803 bp open reading frame which codes for 600 amino acids (SEQ ID NO:13). A piece of 55 bp is possibly the 5' non-coding region and a piece of 206 bp shows the 3' non-coding region, including a poly(A)tail. A hexanucleotide AATAAA consensus signal for polyadenylation is found 20 nucleotides before the poly(A)tail. The nucleotides coding for the $NH_2$ terminal amino acid sequence are found 273 bp from the initiator codon, which indicates that the protein is synthesized as a preprotein (600 amino acids with a calculated molecular mass of 67,829 Da). The resulting mature protein of 509 amino acids has a calculated molecular mass of 57,837 Da and a theoretical pI-value of 6.85. The number of acidic (Glu and Asp) and basic amino acids (His, Lys and Arg) is respectively 74 and 83. A putative mitochondrial signal peptide is present.

DNA sequence determinations were carried out in accordance with the protocols of US Biochemical Corp. Starting sequences were obtained with the use of T7 and T3 vector primers. Specific primers were used to complete the sequences on both strands of cDNA. The sequence analyses were performed with software from the Genetics Computer Group (Madison, Wis., USA).

Example 4

Expression in Yeast

The GLDase cDNA was expressed in *Saccharomyces cerevisiae*. For this purpose the Bluescript vector containing the complete cDNA was digested with ApaI and KpnI and a 27 bp adaptor containing an NotI restriction site was ligated in the vector linearized with ApaI and KpnI. The resulting construct contains two NotI restriction sites and was cloned in the NotI restriction sites of the pFL61 vector (Minet et al., Plant J. 2:417–422 (1992)). Yeast cells of the strain W303A (Matα, ade 2-1, ura 3-1, his 3-11, 15, trp 1-1, leu 2-3, kan$^r$) were transformed by means of the method of Dohmen et al., Yeast 7:691–692 (1991) and plated on selective 1.5% agar plates (without uracil) with minimal SD medium (0.2% yeast nitrogen basis (Difco, Detroit, Mich., USA), 0.7% ammonium sulphate, 2.7% glucose) supplemented with adenine, tryptophan, leucine at a final concentration of 20 µg/ml, and histidine at a final concentration of 10 µg/ml. Transformed cells were transferred to liquid SD medium (as above but without the agar) and cultured for 3 days at 30° C.

The GLDase cDNA was introduced both in the sense orientation and in the antisense orientation relative to the PGK (phosphoglycerate kinase) promoter and terminator. Non-transformed and transformed yeasts were grown and extracts were prepared and tested for GLDase activity. Extracts of yeasts which had been transformed with a sense-oriented GLDase cDNA displayed a three- to six-fold increase in specific GLDase activities compared with extracts from non-transformed yeast and yeast which had been transformed with antisense-oriented GLDase cDNA. Wild type yeast has no endogenous GLDase activity. For determination of protein levels and GLDase activity, cells were harvested by centrifugation (18,000 g, 15 min.), washed and resuspended in 50 mM Tris-HCl (pH 8.0) and disrupted in a French press.

Example 5

Transformation of Arabidopsis and Tobacco

1. Introduction

The GLDase cDNA clone has been used to make sense and antisense GLDase constructs under control of the 35S cauliflower Mosaic Virus (CaMV) promoter. Agrobacterium-mediated transformation has been used to produce transgenic arabidopsis and tobacco plants with the engineered antisense and sense GLDase constructs in order to down-regulate or to up-regulate the GLDase transcript, respectively. Increased GLDase activity was observed in plants transformed with a sense-orientated GLDase cDNA, whereas the specific GLDase activity was low in several antisense plant-lines (see table 4). As a consequence decreased ascorbic acid (AA) levels were measured in antisense transformed plant-lines (see table 5).

2. Materials and Methods

2.1. Plasmids and Vectors

The GLDase cDNA was inserted in both orientations into the pLBR19 vector (Leple et al. (1992), supra) containing the cauliflower mosaic virus (CaMV) 35S promoter with a double enhancer sequence (CaMV 70). The promoter, enhancer and GLDase cDNA were then cloned into the binary vector pBIN19 (Frisch et al. (1995), supra), which carries an additional neomycin phosphotransferase (nptII) gene under control of the CaMV 35S promoter.

The sense construct was made as follows: the GLDase cDNA contained in a Bluescript vector was cut with PstI and the resulting partial GLDase cDNA was cloned into the PstI cloning site of the pLBR19 vector in the sense orientation, followed by excision of a SalI-ClaI fragment of this construct. The remaining part of the GLDase cDNA was then inserted as a XhoI-ClaI fragment, resulting in a pLBR19 vector containing the complete GLDase cDNA sequence.

For the antisense construct the following procedure was followed: a fragment of the Bluescript inserted GLDase cDNA was generated by XhoI digestion and inserted into the SalI site of the pLBR19 vector in antisense orientation. Then a SmaI-NsiI fragment was excised from this construct and the remaining part of the GLDase cDNA was inserted as a SmaI-NsiI fragment resulting in a pLBR19 vector containing the complete GLDase in antisense orientation. The promoter, enhancer, and GLDase cDNA (sense and antisense orientation) were finally cloned into the KpnI-XbaI site of the binary vector pBIN19.

The binary plasmids were then mobilized into Agrobacterium, strain C58 Rif (pMP90) as described by Zham et al., Mol. Gen. Genet. 194:188–194 (1984).

DNA electrophoresis, endonuclease digests, ligation reactions and *Escherichia coli* (strain DH5α) transformations were performed as according to Sambrook et al. (1989), supra.

2.2. Transformation and Regeneration

MP90 *Agrobacterium tumefaciens* (strain C58 Rif) were grown with rifampicin (50 mg/ml), gentamicin (100 mg/l) and kanamycin (200 mg/l) prepared as described by Bechtold et al. (1993), supra and used for plant infection.

2.3. Arabidopsis

*Arabidopsis thaliana* (columbia cultivar) plants were grown on soil, under standard greenhouse conditions. The plants were transformed by vacuum infiltration as described by Bechtold et al. (1993), supra.

2.4. Tobacco

Transgenic plants were produced from leaf discs of *Nicotiana tabacum* (SR1) following Agrobacterium-mediated transformation as modified by Thomas et al. (1990), supra. Co-cultivation was for 2–3 days in basal medium (BM) containing 0.5 µM 1-naphtaleneacetic acid and 2.5 µM 6-benzylaminopurine. Leaf discs were then transferred to BM supplemented with the phytohormones mentioned above, and 100 mg/ml kanamycin (Sigma, St. Louis, Mo.) and 500 mg/l carbenicillin (Sigma). Shoots that formed after 4 weeks were rooted in phytohormone-free BM containing kanamycin.

Plants were transferred to soil, grown under standard greenhouse conditions and self-pollinated. Mature seeds were collected and selected by germination in the presence of kanamycin (125 mg/l).

2.5. Protein Extraction

Extracts from plants were prepared by grinding 7 g fresh tissue in liquid nitrogen. Four volumes of buffer containing 100 mM sodium phosphate (pH 7.4) containing 400 mM sucrose were added. The homogenate was squeezed through four layers of Miracloth tissue and centrifuged at 22,000×g for 30 min. The pellet was resuspended in 5 ml 100 mM sodium phosphate (pH 7.4). Cold acetone (50 ml, −20° C.) was slowly added under stirring and the mixture allowed to stand for 30 min. at 40° C. The precipitated protein was collected by centrifugation (10,000×g for 15 min.). The pellet was dried under vacuum for 30 min. and resuspended in 0.5 ml 40 mM Tris-HCl buffer (pH 8.5). Insoluble proteins were removed by centrifugation (10,000×g for 15 min.). This preparation was desalted by gelfiltration on pre-packed NAP-10 (Pharmacia) and used for GLDase activity assays.

2.6. Screening of a Genomic Library Prepared by *Arabidopsis thaliana*

For screening of a genomic library of *Arabidopsis thaliana*, the GLDase cDNA was radiolabelled and used as a probe. Five positive clones were isolated. DNA from the largest of these five clones was digested with several restriction enzymes and fractionated on 0.8% (w/v) agarose gel and blotted onto a Hybond-N+ membrane (Amersham, USA) as recommended by Amersham. DNA fragments which hybridized to the GLDase cDNA probe were subcloned into pbluescript KS(+) (Stratagene, USA) and sequenced.

3. Results 3.1. Analysis of Plants

Transformed plants were found with the positive (sense) orientation of the GLDase cDNA, and these contained GLDase activity at 2 to 3-fold higher levels, as compared to control plants. In the plants transformed with the GLDase cDNA in a negative (anti-sense) orientation, GLDase activity was approximately 25% of the control plants.

The ascorbic acid levels of 28 antisense GLDase plants were generally lower than the control plants. One plant had 35% AA content compared to the controls and several other plants have values around 50%. The AA levels of the sense GLDase plants were generally higher compared to the controls, with one line attaining 134% of the control.

3.2. Isolation of GLDase Gene from Arabidonsis

By screening a genomic Arabidonsis library a 3117 bp DNA clone was isolated. Comparison with the GLDase cDNA sequence isolated from cauliflower indicated that the genomic contained 6 introns. The isolated clone contains 260 bp of the promoter region up-stream to the first ATG (start) codon. The sequence which corresponds to the last 260 bp from the 3'-end of the GLDase cDNA was not found (FIG. 5). The nucleotide sequence corresponds to SEQ ID NO:14 and the amino acid sequence is SEQ ID NO:15.

4. Conclusions

The results show the presence of a correctly processed and biologically active GLDase cDNA in the transgenic tobacco plants. It was possible to measure increased GLDase activity levels in plants transformed with GLDase cDNA in the sense orientation. Furthermore, a decreased GLDase activity was measured in plants transformed with the corresponding cDNA in the antisense orientation. In these plants lower ascorbic acid levels were measured.

Leaf disc assays did not conclusively show if transformed plants have changed oxidative stress tolerance.

TABLE 4 enzyme assays transformed tobacco

| plants | total activity (units/min.) | specific activity (units/min. × mg protein) | % |
|---|---|---|---|
| control | 6.0 | 1.8 | 100% |
| sense | 5.6 | 2.1 | 117% |
| sense | 2.2 | 3.7 | 206% |
| sense | 10.5 | 3.0 | 167% |
| antisense | 2.6 | 0.5 | 28% |
| antisense | 1.3 | 0.4 | 22% |

TABLE 5

Anti-oxidant status of transgenic Nicotiana in nmoles/gram fresh weight

| plants | L-AA | L-DHA | total |
|---|---|---|---|
| control | 1135 | 132 | 1267 (100%) |
| sense | 1550 | 152 | 1702 (134%) |
| antisense | 520 | 34 | 554 (44%) |

L-AA = ascorbic acid
L-DHA = oxidized L-AA (dehydro-ascorbic acid)

Example 6

Expression in Murine Fibrosarcoma Cells

Figure 4:
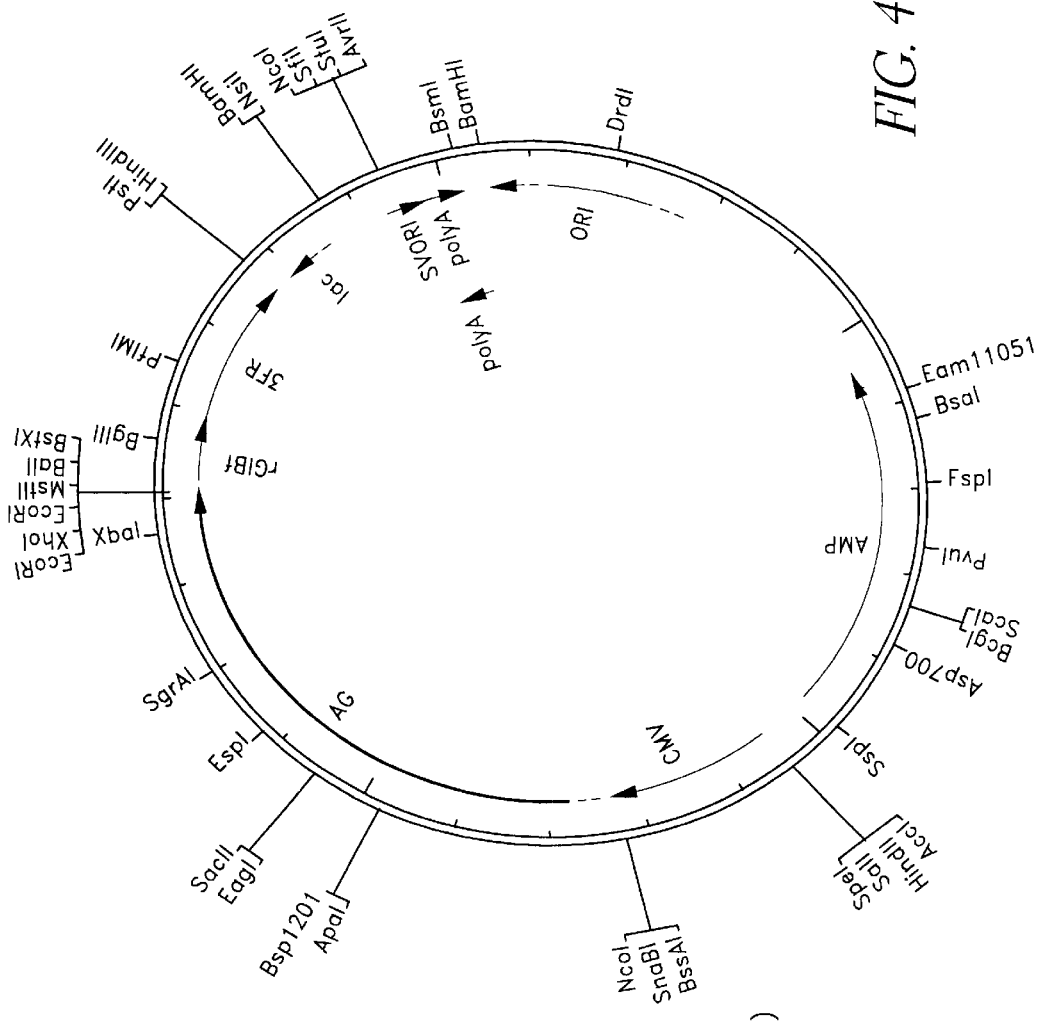
FIG. 4 is a plasmid map of pCAGGS used for cloning of L-galactono-γ-lactone dehydrogenase cDNA.

1. Construction of the Eukaryotic Expression Vector pCAGGS/L-galactono-γ-lactone Dehydrogenase pCAGGS is an expression vector which is used for the efficient expression of genes under the control of the chicken β-actin/rabbit β-globin hybrid promoter+CMV-IE enhancer in different mammalian cells (FIG. 4). The plasmid is a gift from Prof. J. Miyazaki (University or Tokyo, Japan) (Niwa et al., Gene 108:193–200 (1991)).

The L-galactono-γ-lactone dehydrogenase gene was isolated after digestion of the Bluescript SK vector with XbaI and KpnI. The KpnI site was blunted with T4 DNA polymerase and the XbaI/blunt fragment was cloned into the XbaI/BalI sites of the pCAGGS vector. The XbaI site of the pCAGGS is situated at the end of the actual. promoter, but the use of this site for cloning a gene has no effect on the expression efficiency.

2. Transfection Procedure: Stable Transfection Via DNA Calcium Phosphate Precipitation Technique 2.1. Preparation of the Cells 28 hours before transfection, L929sA murine fibrosarcoma cells are placed in culture at a concentration of $2.10^6$ cells per culture bottle of 75 cm². The culture medium used is Dulbeccols modified essential medium (DMEM) enriched with 5% foetal calf serum (FCS), 5% newborn calf serum (NCS), 3 mM glutamine and the antibiotics streptomycin and penicillin. The culture conditions used are 37° C., 5% $CO_2$.

4 hours before transfection the culture medium is replaced by 10 ml HEPES-buffered minimum essential medium (MEM-HEPES) enriched with 10% FCS, 3 mM glutamine and antibiotics.

2.2. Preparation of DNA Precipitate

DNA calcium phosphate precipitate is prepared by adding 30 μg DNA (in 0.25 M $CaCl_2$/0.125 M HEPES pH 7.05) to the same volume 2× concentrated phosphate/HEPES buffer (0.25 M HEPES, 0.27 M NaCl, 6.7 mM CaCl$_2$, 1.5 mM Na$_2$HPO$_4$). The 30 μg DNA is composed from 19 μg carrier DNA irrelevant plasmid DNA)+1 μg DNA of the selection plasmid (pSV2 neoplasmid carrying the neomycin resistance gene)+10 μg pCAGGS/L-galactono-γ-lactone dehydrogenase (plasmid with relevant gene).

2.3. Transfection

The DNA precipitate is placed together with 10 μM chloroquine on the cells, and the mixture incubated for 4 hours in 5% CO$_2$ at 37° C. The medium with DNA is then removed from the cells and the cells are further held in culture with DMEM.

2.4. Growth and Isolation of Individual Cell Colonies

The following day the transfected cells are diluted to a concentration of 250,000 cells per culture bottle of 75 cm$^2$ and these are further held in culture through selection with the antibiotic G418. After 10–12 days individual colonies can be picked up out of the culture bottle.

The selected colonies are cultured and analyzed for expression of the L-galactono-γ-lactone dehydrogenase. The clones designated with V3, V6, V8 and V14 were found to be positive for the expression of the L-galactono-γ-lactone dehydrogenase. The enzyme activities are shown in table 6.

TABLE 6

GLDase activity in transfected murine fibrosarcoma cells.
All values are expressed in specific activity of the
enzyme (units/min./mg protein)

| cell line: | VI pod (control) | 0 |
|---|---|---|
|  | N2 (control) | 0 |
| transfected: | V6 | 3.7 |
|  | V14 | 2.1 |
|  | V3 | 1.4 |
|  | V8 | 2.0 |

TABLE 2

Amino acid sequences determined from the GLDase polypeptide
X refers to amino acid sequences not determined by sequence determining runs. Degenerated oligonucleotides were designed on the basis of peptides 1, 4 and 7.

Peptide sequences obtained from 55 kDa polypeptide after tryptic digestion

NH$_2$-terminal sequences

YAPLXEDL (SEQ ID NO.9)

Internal sequences

LXDQYSAYE (SEQ ID NO (1)
VNQAEAEF (SEQ ID NO: (2)
LIALDPLNDVHVG SEQ ID NO: (3)
YTTEEALK SEQ ID NO. (4)
WTGR SEQ ID NO (5)
GTIELSK SEQ ID NO (6)
VNQAEAEFWK SEQ ID NO (7)
IEIPK SEQ ID NO (8)

Peptide sequences obtained from 31 kDa and 26 kDa subdivisions

NH$_2$-terminal sequences

APLPDLHTVSN (30 kDa) SEQ ID NO
XSSKKTPDXRXPDINXL (26 kDa) SEQ ID NO

TABLE 1

Purification diagram for GLDase
A mitochondrial extract of 15 kg cauliflower florets was used for the preparation.

| STEP | VOL. (ml) | PROTEIN (mg) | TOTAL ACTIVITY units | SPECIFIC ACTIVITY units/mg | -FOLD | YIELD % |
|---|---|---|---|---|---|---|
| Acetone prec. | 2500 | 1510 | 44,900 | 30.5 | 1 | 100 |
| DEAE ion exchanger | 83 | 54.7 | 46,500 | 845 | 28 | 104 |
| Phenyl Sepharose | 38 | 21.2 | 30,800 | 1,467 | 49 | 69 |
| Gel filtration | 54 | 10.5 | 20,900 | 1,900 | 63 | 47 |
| FPLC Resource Q | 32 | 0.3 | 8,100 | 2,700 | 900 | 18 |
| FPLC Poros 20 SP | 4 | 0.01 | 508 | 50,800 | 1693 | 1.1 |

What is claimed is:

1. An isolated or purified cDNA comprising SEQ ID NO:12 or fragment thereof encoding a polypeptide having L-galactono-γ-lactone dehydrogenase activity.

2. The isolated or purified cDNA as claimed in claim 1, consisting essentially of SEQ ID NO:12.

3. A recombinant expression vector comprising the isolated or purified cDNA of claim 1.

4. A recombinant expression vector comprising SEQ ID NO:12.

5. The recombinant expression vector of claim 3 further comprising a polynucleotide coding for transcription and/or translation regulation factors.

6. The recombinant expression vector of claim 3 further comprising a targeting sequence for targeting the encoded enzyme to various parts of a cell.

7. The recombinant expression vector of claim 6, wherein the parts of the cell are selected from the group consisting of: the cytoplasm, vacuoles, chloroplasts, mitochondria, lysosomes, endoplasmic reticulum, and Golgi apparatus.

8. An isolated or purified cDNA comprising SEQ ID NO:14 or fragment thereof encoding a polypeptide having L-galactono-γ-lactone dehydrogenase activity.

9. An isolated or purified polynucleotide encoding an amino acid sequence comprising SEQ ID NO:13 or a fragment thereof having L-galactono-γ-lactone dehydrogenase activity.

10. An isolated or purified polynucleotide encoding an amino acid sequence comprising SEQ ID NO:15 or a fragment thereof having L-galactono-γ-lactone dehydrogenase activity.

11. An isolated or purified cDNA comprising SEQ ID NO:12 or a fragment thereof encoding an amino acid sequence having L-galactono-γ-lactone dehydrogenase activity, with the proviso that said cDNA does not encode an amino acid sequence selected from the group consisting of: LTQAK; SKSPMSPAFSTA; DLYR; YTTEEALK; IEIP-KDKEELEALQE; VNQAEAEF; DLEYIEQLK; DLCYIEQLK; YAPLDEDLHTVSNW; YLYIPYTDTV- VVVT; NFNQPETLADLEALVK; VGWSXEELGFDXG-GQQXV; VQQLVDAIQEYGL; EQQLGGLLQV-GAXGTGA; YKENELNMGENS; and LKENELNMGENS.

12. The isolated or purified polynucleotide of claim 8, comprising SEQ ID NO:14.

13. A recombinant expression vector comprising the isolated or purified polynucleotide of claim 8.

14. A recombinant expression vector comprising SEQ ID NO:14.

15. The recombinant expression vector of claim 13, further comprising a polynucleotide coding for transcription and/or translation regulation factors.

16. The recombinant expression vector of claim 13 further comprising a targeting sequence for targeting the encoded enzyme to various parts of a cell.

17. The recombinant expression vector of claim 16, wherein the parts of the cell are selected from the group consisting of: the cytoplasm, vacuoles, chloroplasts, mitochondria, lysosomes, endoplasmic reticulum, and Golgi apparatus.

18. An isolated or purified cDNA comprising SEQ ID NO:12 or a sequence derived therefrom on the basis of the degeneration of the genetic code.

19. An isolated or purified cDNA comprising SEQ ID NO:14 or a sequence derived therefrom on the basis of the degeneration of the genetic code.

20. An isolated or purified polynucleotide encoding an amino acid sequence comprising SEQ ID NO:13.

21. An isolated or purified polynucleotide encoding an amino acid sequence comprising SEQ ID NO:15.

22. The isolated or purified cDNA of claim 8, consisting essentially of SEQ ID NO:14.

* * * * *